(12) United States Patent
Watson et al.

(10) Patent No.: US 7,208,579 B2
(45) Date of Patent: Apr. 24, 2007

(54) IL4 RECEPTOR ANTAGONISTS FOR HORSE, DOG AND CAT

(75) Inventors: Johanna L. Watson, Esparto, CA (US); Kenneth A. Jackson, Elk Grove, CA (US)

(73) Assignee: The Regents of the University of California, Oakland, CA (US)

( * ) Notice: Subject to any disclaimer, the term of this patent is extended or adjusted under 35 U.S.C. 154(b) by 64 days.

(21) Appl. No.: 10/857,673

(22) Filed: May 28, 2004

(65) Prior Publication Data
US 2005/0032164 A1    Feb. 10, 2005

Related U.S. Application Data

(60) Provisional application No. 60/561,579, filed on Apr. 12, 2004, provisional application No. 60/475,220, filed on May 30, 2003.

(51) Int. Cl.
*C07K 14/52*   (2006.01)
*C07K 14/715*  (2006.01)

(52) U.S. Cl. .................. 530/351; 424/85.2
(58) Field of Classification Search ............ None
See application file for complete search history.

(56) References Cited

OTHER PUBLICATIONS

Solberg, et al. Vet. Immunol. Immunopathol. 97: 187-194, 2004 'Genomic characterization of equine interleukin-4 receptor alpha-chain (IL4R)'.*

* cited by examiner

*Primary Examiner*—Gary B. Nickol
*Assistant Examiner*—Nirmal S. Basi
(74) *Attorney, Agent, or Firm*—Townsend and Townsend and Crew, LLP

(57) ABSTRACT

The present application provides the horse, cat and dog IL4 receptor, including soluble receptors as well as method for therapeutic use of such receptors.

6 Claims, 17 Drawing Sheets

| | | |
|---|---|---|
| HUMAN | (1) | MGWLCSGLLFPVSCLVLLQVASSGNMKVLQEPTCVSDYMSISTCEWKMNGPTNCSTELRI |
| HORSE | (1) | MGCLCPGLTLPVSCLILVWAAGSGSVKVLRLTACFSDYISASTCEWKMDRPTNCSAQLRL |
| HUMAN | (61) | LYQLVFLLSEAHTCIPENNGGAGCVCHLLMDDVVSADNYTLDLWAGQLLWKGSFKPSEH |
| HORSE | (61) | SYQLNDEFSDNLTCIPENREDEVCVCRMLMDNIVSEDVYFLDLWAGNQLLWNSSFKPSRH |
| HUMAN | (121) | VKPRAPGNLTVHTNVSDTLLLTWSNPYPPDNYLYNHLTYAVNIMSENDPADFRIYNVTYL |
| HORSE | (121) | VKPRAPQNLTVHA-ISHTWLLTWSNPYPLKNHLWSELTYLVNISKEDDPTDFKIYNVTYM |
| HUMAN | (181) | EPSLRIAASTLKSGISYRARVRAWAQCYNTWSEWSPSTKWHNSYREPFEQHLLGVSVS |
| HORSE | (180) | DPTLRVTASTLKSRATYSARVKARAQNYNSTWSEWSPSTTWHNYYFQPLEQRLPLGVSIS |
| HUMAN | (241) | CIVILAVCLLCYVSITKIKKEWWDQIPNPARSRLVAIIIQDAQGSQWEKRSRGQEPAKCP |
| HORSE | (240) | CVVILAICLSCYFSIIKIKKEWWDQIPNPAHSPLVAIVLQDSQVSLWGKQSRGQEPAKCP |

FIG. 1A

Comparison of Horse IL4R and Soluble IL4R amino acid sequences

```
                         1                                                         50
Horse IL4R     (1)   MGCLCPGLTLPVSCLLIVWAAGSGSVKVLRLTACFSDYISASTCEWKMDR
Horse sIL4R    (1)   MGCLCPGLTLPVSCLLIVWAAGSGSVKVLRLTACFSDYISASTCEWKMDR
                        51                                                        100
Horse IL4R    (51)   PTNCSAQLRLSYQLNDEFSDNLTCIPENREDEVCVCRMLMDNIVSEDVYE
Horse sIL4R   (51)   PTNCSAQLRLSYQLNDEFSDNLTCIPENREDEVCVCRMLMDNIVSEDVYE
                       101                                                        150
Horse IL4R   (101)   LDIWAGNQLLWNSSFKPSRHVKPRAPQNLTVHAISHTWLLTWSNPYPLKN
Horse sIL4R  (101)   LDIWAGNQLLWNSSFKPSRHVKPRAPQNLTVHAISHTWLLTWSNPYPLKN
                       151                                                        200
Horse IL4R   (151)   HLWSELTYLVNISKEDDPTDFKIYNVTYMDPTLRVTASTLKSRATYSARV
Horse sIL4R  (151)   HLWSELTYLVNISKEDDPTDFKIYNVTYMDPTLRVTASTLKSRATYSARV
                       201                                                        250
Horse IL4R   (201)   KARAQNYNSTWSEWSPSTTWHNYYEQPLEQRLPLGVSISCVVILAICLSC
Horse sIL4R  (201)   KARAQNYNSTWSEWSPSTTWHNSP-------------------------
                       251                                                        300
Horse IL4R   (251)   YFSIIKIKKEWWDQIPNPAHSPLVAIVLQDSQVSLWGKQSRGQEPAKCPR
Horse sIL4R  (225)   --------------------------------------------------
                       301                                                        350
Horse IL4R   (301)   WKTCLTKLLPCLLEHGLQKEEDSSKTVRNGPFQSPGKSAWHTVEVNHTIL
Horse sIL4R  (225)   --------------------------------------------------
                       351                                                        400
Horse IL4R   (351)   RPEIISVVPCVELCEAQVESEEEEVEEDRGSFCPSPESSGSGFQEGREGV
Horse sIL4R  (225)   --------------------------------------------------
```

FIG. 2A

```
Horse IL4R   (401) AARLTESLFLGLLGAENGALGESCLLPPLGSAHMPWARISSAGPQEAASQ  450
Horse sIL4R  (225) ------------------------------------------------   ---

Horse IL4R   (451) GEEQPLNPESNPLATLTQSPGSLAFTEAPAVVADNPAYRSFSNSLSQPRG  500
Horse sIL4R  (225) ------------------------------------------------   ---

Horse IL4R   (501) PGELDSDPQLAEHLGQVDPSIPSAPQPSEPPTALQPEPETWEQMLRQSVL  550
Horse sIL4R  (225) ------------------------------------------------   ---

Horse IL4R   (551) QQGAAPAPASAPTGGYREFAQVVKQGGAAGSGPSGEAGYKAFSSLLAGS   600
Horse sIL4R  (225) ------------------------------------------------   ---

Horse IL4R   (601) AVCPGQSGVEASSGEGGYRPYESPDPGAPAPVPVPLFTFGLDVEPPHSPQ  650
Horse sIL4R  (225) ------------------------------------------------   ---

Horse IL4R   (651) NSLLPGGSPELPGPEPTVKGEDPRKPLLSAQQATDSLRDDLGSGIVYSAL  700
Horse sIL4R  (225) ------------------------------------------------   ---

Horse IL4R   (701) TCHLCGHLKQCHGQEEHGEAHTVASPCCGCCCGDRSSPPVSPVRALDPPP  750
Horse sIL4R  (225) ------------------------------------------------   ---

Horse IL4R   (751) GGVPLEAGLSLASLGSLGLSEERKPSLFFQPAPGNAQSSSQTPLTVAMLS  800
Horse sIL4R  (225) ------------------------------------------------   ---

Horse IL4R   (801) TGPTCTSAS
Horse sIL4R  (225) ---------
```

FIG. 2B

```
   1 GGGCGCTGCC GAGCCTGGCT GCCCTGGATC CCGCACTTCC CGCTCGGGCG
  51 CTGGACGGCG AATGGGCCAG GGGCGCGCAG GTGCAGTAGG GTCTCCCAAT
 101 GGGGTGCCTT TGCCCCGGGC TCACGCTCCC TGTGAGCTGC CTGATCCTGG
 151 TGTGGGCGGC AGGCTCTGGG AGCGTTAAGG TCCTGCGTCT CACCGCCTGC
 201 TTCTCCGACT ACATCAGCGC CTCCACCTGT GAGTGGAAGA TGGACCGTCC
 251 CACCAACTGC AGTGCCCAGC TCCGTCTGTC CTACCAGCTG AACGACGAGT
 301 TCTCTGACAA CCTCACGTGT ATCCCCGAGA ACAGAGAAGA TGAAGTGTGC
 351 GTGTGCCGTA TGCTGATGGA CAACATCGTC AGCGAGGACG TCTATGAGCT
 401 GGACCTGTGG GCTGGGAACC AACTGCTGTG GAACAGCTCC TTCAAGCCCA
 451 GCCGGCACGT GAAACCCAGG GCCCCTCAAA ACCTCACGGT TCACGCCATC
 501 TCCCACACGT GGCTGCTGAC GTGGAGCAAC CCGTACCCTT TGAAGAATCA
 551 CCTGTGGTCT GAGCTTACCT ACCTGGTCAA CATCTCCAAG GAGGACGACC
 601 CCACGGACTT CAAAATCTAC AACGTGACCT ACATGGACCC CACCCTCCGC
 651 GTCACAGCCA GCACCCTGAA GTCCAGGGCT ACGTACAGCG CACGGGTGAA
 701 GGCCAGGGCT CAGAACTACA ACAGCACCTG GAGTGAGTGG AGCCCCAGCA
 751 CCACGTGGCA TAACTCCCCC TGAACTCTAT CTGCAGCCTT GCTGGAAGTC
 801 TGTGGACCCC GAGTTAAGAT TTCTGCTCTG GCACTGCCA TCATCTGCAT
 851 CCAGGCAGCA GAAGGGGGAA GGAGAGCAGG GAGACCAAAC CCGCTTCTTA
 901 AAAGCCTCAG CCCAGAAGTG ACGCACGTCA CTTCCTCTCA GGTTCTGTTG
 951 GTGAAATTGG TCACGTGGCT ACATGTAGCT GCAAGGGATT CTGGGAAATG
1001 TAGTCCCTCA CTTGGTAGCT GCACCCGCCC CCCCAGTAA CTCTTTACAG
1051 ATCTATCACA CATGGCTTTT GCAATAAAAA
```

FIG. 4A

```
  1 MGCLCPGLTL PVSCLILVWA AGSGSVKVLR LTACFSDYIS ASTCEWKMDR
 51 PTNCSAQLRL SYQLNDEFSD NLTCIPENRE DEVCVCRMLM DNIVSEDVYE
101 LDLWAGNQLL WNSSFKPSRH VKPRAPQNLT VHAISHTWLL TWSNPYPLKN
151 HLWSELTYLV NISKEDDPTD FKIYNVTYMD PTLRVTASTL KSRATYSARV
201 KARAQNYNST WSEWSPSTTW HNSP*
```

FIG. 4B

```
   1 CTCCCAATGG GGTGGCTTTG CTCTGGGCTC ACATTCCCTG TGAGCTGCCT
  51 GGTCCTGGTG TGGGTGGCCA GCTCTGGGAG TGTGAAGGTC CTGCACGAGC
 101 CCAGCTGCTT CTCCGACTAC ATCAGCACCT CTGTCTGTCA GTGGAAGATG
 151 GACCATCCCA CCAACTGCAG TGCCGAGCTC CGCCTGTCCT ACCAGCTGGA
 201 CTTTATGGGG TCTGAAAACC ACACGTGTGT CCCTGAGAAC CGAGAAGACT
 251 CAGTGTGCGT GTGCAGCATG CCGATAGATG ACGCGGTGGA AGCGGATGTC
 301 TATCAGCTGG ACCTGTGGGC TGGGCAGCAG CTGCTATGGA GCGGCTCTTT
 351 CCAGCCCAGC AAGCATGTGA AGCCCAGGAC CCCCGGCAAC CTCACAGTTC
 401 ACCCCAACAT CTCCCACACG TGGCTGCTGA TGTGGACAAA CCCATACCCT
 451 ACTGAGAATC ACCTGCACTC TGAGCTCACC TACATGGTCA ACGTTTCGAA
 501 TGACAACGAC CCCGAGGACT TTAAAGTCTA TAATGTGACC TACATGGGGC
 551 CCACCCTCCG CTTGGCAGCC AGCACCCTCA AGTCTGGAGC TTCCTACAGC
 601 GCACGTGTGA GGGCCTGGGC TCAGACCTAC AACAGCACCT GGAGTGATTG
 651 GAGCCCCAGC ACCAGGTGGC TTAACTACTA CGAGCCCTGG GAGCAGCACC
 701 TGCCACTTGG CGTCAGCATC TCCTGCCTCG TCATCCTGGC CATCTGCCTG
 751 TCCTGCTACT TCAGTATCAT CAAGATTAAG AAAGGATGGT GGGATCAGAT
 801 TCCCAACCCA GCCCACAGCC CCTCGTGGC CATAGTCATC CAGGACTCAC
 851 AGGTGTCGCT CTGGGGAAG CGGTCCCGAG GCCAGGAACC AGCCAAGTGC
 901 CCACACTGGA AGACTTGTCT TACCAAGCTC CTGCCCTGTC TACTGGAGCA
 951 TGGCCTGGGC AGGGAGGAGG AGTCCCCCAA GACTGCCAAA AATGGGCCTC
1001 TCCAAGGTCC TGGAAAACCC GCGTGGTGCC CTGTGGAGGT CAGCAAGACG
1051 ATC
```

FIG. 5

```
   1  CTCCCAATGG GGTGGCTTTG CTCTGGGCTC ACATTCCCTG TGAGCTGCCT
  51  GGTCCTGGTG TGGGTGGCCA GCTCTGGGAG TGTGAAGGTC CTGCACGAGC
 101  CCAGCTGCTT CTCCGACTAC ATCAGCACCT CTGTCTGTCA GTGGAAGATG
 151  GACCATCCCA CCAACTGCAG TGCCGAGCTC CGCCTGTCCT ACCAGCTGGA
 201  CTTTATGGGG TCTGAAAACC ACACGTGTGT CCCTGAGAAC CGAGAAGACT
 251  CAGTGTGCGT GTGCAGCATG CCGATAGATG ACGCGGTGGA AGCGGATGTC
 301  TATCAGCTGG ACCTGTGGGC TGGGCAGCAG CTGCTATGGA GCGGCTCTTT
 351  CCAGCCCAGC AAGCATGTGA AGCCCAGGAC CCCCGGCAAC CTCACAGTTC
 401  ACCCCAACAT CTCCCACACG TGGCTGCTGA TGTGGACAAA CCCATACCCT
 451  ACTGAGAATC ACCTGCACTC TGAGCTCACC TACATGGTCA ACGTTTCGAA
 501  TGACAACGAC CCCGAGGACT TTAAAGTCTA TAATGTGACC TACATGGGGC
 551  CCACCCTCCG CTTGGCAGCC AGCACCCTCA AGTCTGGAGC TTCCTACAGC
 601  GCACGTGTGA GGGCCTGGGC TCAGACCTAC AACAGCACCT GGAGTGATTG
 651  GAGCCCCAGC ACCAGGTGGC TTAACTACAC CTCCTCTGGC TGAGCATCCG
 701  TGTTTTGCAT TCCCATAGCA GAGAGTGGCT CTAACTGTGG GTTAATGGGA
 751  TTACTGACTG ACCTGGTGTA CTGGTCAGGG CAGGTAGGGC AGGCTGCGGT
 801  AACAAATGAG CCCGCAAGTT CTGTGACTCT TCGCTGTAGG AATGTATTTC
 851  TTGGTCATGT AACCGTCCAG CGTGAACTCA GCTGGTTTTG CAGGGATGGG
 901  GGAGGGGGGC TCCTCCCTGT GGTTCCATCA TTCCCTTAGG GACAAAGATT
 951  CCTAACCTTT TCATATCATG GACCCCTTTG GCTGTGAACC CCAGAATACT
1001  ATTTTTAAAT GTAAAAAATA AAAT
```

FIG. 6

```
  1 MGWLCSGLTF PVSCLVLVWV ASSGSVKVLH EPSCFSDYIS TSVCQWKMDH
 51 PTNCSAELRL SYQLDFMGSE NHTCVPENRE DSVCVCSMPI DDAVEADVYQ
101 LDLWAGQQLL WSGSFQPSKH VKPRTPGNLT VHPNISHTWL LMWTNPYPTE
151 NHLHSELTYM VNVSNDNDPE DFKVYNVTYM GPTLRLAAST LKSGASYSAR
201 VRAWAQTYNS TWSDWSPSTR WLNYYEPWEQ HLPLGVSISC LVILAICLSC
251 YFSIIKIKKG WWDQIPNPAH SPLVAIVIQD SQVSLWGKRS RGQEPAKCPH
301 WKTCLTKLLP CLLEHGLGRE EESPKTAKNG PLQGPGKPAW CPVEVSKTIL
351 WPESISVVQC VELSEAPVDN EEEEEVEEDK RSLCPSLEGS GGSFQEGREG
401 IVARLTESLF LDLLGGENGG FCPQGLEESC LPPPSGSVGA QMPWAQFPRA
451 GPRAAPEGPE QPRRPESALQ ASPTQSAGSS AFPEPPPVVT DNPAYRSFGS
501 FLGQSSDPGD GDSDPELADR PGEADPGIPS APQPPEPPAA LQPEPESWEQ
551 ILRQSVLQHR AAPAPGPGPG SGYREFTCAV KQGSAPDAGG PGFGPSGEAG
601 YKAFCSLLPG GATCPGTSGG EAGSGEGGYK PFQSLTPGCP GAPTPVPVPL
651 FTFGLDTEPP GSPQDSLGAG SSPEHLGVEP AGKEEDSRKT LLAPEQATDP
701 LRDDLASSIV YSALTCHLCG HLKQWHDQEE RGKAHIVPSP CCGCCCGDRS
751 SLLLSPLRAP NVLPGGVLLE ASLSPASLVP SGVSKEGKSS PFSQPASSSA
801 QSSSQTPKKL AVLSTETTCM SAS*
```

FIG. 7

```
  1    MGWLCSGLTF  PVSCLVLVWV  ASSGSVKVLH  EPSCFSDYIS  TSVCQWKMDH
 51    PTNCSAELRL  SYQLDFMGSE  NHTCVPENRE  DSVCVCSMPI  DDAVEADVYQ
101    LDLWAGQQLL  WSGSFQPSKH  VKPRTPGNLT  VHPNISHTWL  LMWTNPYPTE
151    NHLHSELTYM  VNVSNDNDPE  DFKVYNVTYM  GPTLRLAAST  LKSGASYSAR
201    VRAWAQTYNS  TWSDWSPSTR  WLNYTSSG*
```

FIG. 8

```
  1   MGRLCSGLTF  PVSCLILMWA  AGSGSVKVLR  APTCFSDYFS  TSVCQWNMDA
 51   PTNCSAELRL  SYQLNFMGSE  NRTCVPENGE  GAACACSMLM  DDFVEADVYQ
101   LHLWAGTQLL  WSGSFKPSSH  VKPRAPGNLT  VHPNVSHTWL  LRWSNPYPPE
151   NHLHAELTYM  VNISSEDDPT  DSRIYNVTYM  GPTLRVAAST  LTSGASYSAR
201   VRAWAQSYNS  TWSEWSPSTK  WLNHYEPWEQ  HLPLGVSISC  LVILAVCLSC
251   YLSVIKIKKE  WWDQIPNPAH  SHLVAIVIRD  PQVSLWGKRS  RGQEPAKCPH
301   WKTCLRKLLP  CLLEHGMERK  EDPSKIARNG  PSQCSGKSAW  CPVEVSKTIL
351   WPESISVVRC  VELLEAPVES  EEEEEEEED   KGSFCPSPVN  LEDSFQEGRE
401   GIAARLTESL  FMDLLGVEKG  GFGPQGSLES  WFPPPSGSAG  AQMPWAEFPG
451   PGPQEASPQG  KEQPFDPRSD  PLATLPQSPA  SPTFPETPPV  VTDNPAYRSF
501   GTFQGRSSGP  GECDSGPELA  GRLGEADPGI  PAAPQPSEPP  SALQPEAETW
551   EQILRQRVLQ  HRGAPAPAPG  SGYREFVCAV  RQGSTQDSRV  GDFGPSEEAG
601   YKAFSSLLTS  GAVCPETSGG  EAGSGDGGYK  PFQSLTPGCP  GAPAPVPVPL
651   FTFGLDAEPP  HCPQDSPLPG  SSPEPAGKAQ  DSHKTPPAPE  QAADPLRDDL
701   ASGIVYSALT  CHLCGHLKQC  HGQEEGGEAH  PVASPCCGCC  RGDRSSPLVS
751   PLRAPDPLPG  GVPLEASLSP  ASPAPLAVSE  EGPPSLCFQP  ALSHAHSSSQ
801   TPKKVAMLSP  EPTCTMAS*
```

FIG. 9

```
  1  MGRLCSGLTF PVSCLILMWA AGSGSVKVLR APTCFSDYFS TSVCQWNMDA
 51  PTNCSAELRL SYQLNFMGSE NRTCVPENGE GAACACSMLM DDFVEADVYQ
101  LHLWAGTQLL WSGSFKPSSH VKPRAPGNLT VHPNVSHTWL LRWSNPYPPE
151  NHLHAELTYM VNISSEDDPT DSRIYNVTYM GPTLRVAAST LTSGASYSAR
201  VRAWAQSYNS TWSEWSPSTK WLN
```

FIG. 10

```
   1 ATCCCGCTCG GGCGCGGGCG CGGCGAATGG ACCCGGGGCG CGCAGGTGTC
  51 TTAGGATCTC CCAATGGGGC GGCTTTGCTC TGGGCTCACG TTCCCTGTGA
 101 GCTGTCTGAT CCTGATGTGG GCGGCAGGCT CTGGGAGCGT CAAGGTCCTG
 151 CGTGCGCCCA CCTGCTTCTC CGACTACTTC AGCACCTCCG TCTGCCAGTG
 201 GAACATGGAT GCGCCCACGA ACTGCAGCGC TGAGCTCCGC CTGTCCTACC
 251 AGCTGAACTT CATGGGGTCC GAAAACCGCA CGTGTGTCCC TGAGAACGGA
 301 GAAGGCGCGG CGTGTGCGTG CAGCATGCTG ATGGACGACT TTGTCGAAGC
 351 GGACGTGTAT CAGCTGCACC TGTGGGCGGG GACGCAGCTG CTGTGGAGCG
 401 GCTCCTTCAA GCCCAGCAGT CACGTGAAAC CCAGGGCTCC CGGAAACCTC
 451 ACGGTTCACC CCAACGTCTC CCACACGTGG CTGCTGAGGT GGAGCAACCC
 501 TTACCCCCCT GAGAACCACC TGCACGCCGA GCTCACCTAC ATGGTCAACA
 551 TCTCGAGTGA AGACGACCCC ACGGATTCCA GAATCTATAA TGTGACCTAC
 601 ATGGGGCCCA CCCTCCGCGT GGCAGCCAGC ACCCTGACGT CTGGGCTTC
 651 CTACAGCGCA CGCGTGAGGG CCTGGGCTCA GAGCTACAAC AGCACCTGGA
 701 GCGAGTGGAG CCCCAGCACC AAGTGGCTTA **ACCACTACGA GCCCTGGGAG
 751 CAGCACCTCC CACTTGGCGT CAGCATCTCC TGCCTTGTCA TCCTGGCCGT
 801 CTGCCTGTCC TGCTACCTCA GCGTCATCAA** GATTAAGAAA GAATGGTGGG
 851 ACCAGATTCC CAACCCCGCC CACAGCCACC TAGTGGCGAT AGTCATCCGG
 901 GACCCACAGG TGTCGCTGTG GGGGAAGCGG TCCCGAGGCC AGGAACCAGC
 951 CAAGTGCCCA CACTGGAAGA CTTGTCTTAG GAAGCTCCTG CCCTGTTTAC
1001 TGGAGCACGG CATGGAAAGG AAAGAGGATC CCTCCAAGAT TGCCAGAAAT
1051 GGGCCTTCGC AGTGTTCTGG AAAATCAGCA TGGTGCCCCG TGGAGGTCAG
1101 CAAGACGATC CTCTGGCCCG AGAGCATCAG TGTGGTGCGA TGTGTGGAGC
1151 TCCTGGAGGC CCCGGTGGAG AGCGAGGAGG AGGAGGAGGA GGAGGAGGAA
1201 GATAAAGGGA GCTTCTGCCC ATCGCCTGTG AACCTCGAGG ACAGCTTCCA
1251 GGAGGGCCGG GAGGGCATCG CGGCCCGGCT GACCGAAAGC CTCTTCATGG
1301 ACCTTCTCGG GGTTGAGAAA GGGGGCTTTG CCCACAGGG CTCGCTGGAA
1351 TCGTGGTTTC CTCCTCCTTC GGGAAGTGCA GGTGCTCAGA TGCCCTGGGC
1401 TGAGTTTCCG GGTCCGGGGC CCCAGGAGGC ATCGCCCCAG GGCAAGGAGC
1451 AGCCTTTCGA CCCCCGGTCC GATCCTCTGG CCACTCTGCC CAGAGCCCA
1501 GCCAGCCCGA CTTTCCCAGA GACGCCCCCG GTCGTCACAG ACAACCCCGC
1551 CTACCGCAGC TTCGGGACCT TCAGGGCCG GTCCTCAGGT CCCGGCGAGT
1601 GTGACTCGGG CCCCGAGCTG GCGGGACGCC TGGGGGAGGC GGACCCTGGC
1651 ATCCCCGCTG CCCCCCAGCC TTCGGAGCCG CCTTCCGCGC TCCAGCCCGA
1701 GGCAGAGACC TGGGAGCAGA TTCTGCGTCA GCGAGTCCTG CAGCACAGGG
1751 GGGCCCCGGC CCCGGCCCCC GGCAGCGGCT ACCGAGAGTT TGTGTGCGCC
1801 GTGAGGCAGG GCAGCACCCA GGACAGCAGG GTGGGGGACT TCGGCCCCTC
1851 GGAGGAGGCC GGGTACAAGG CCTTCTCGAG TCTGCTCACT AGCGGTGCCG
1901 TCTGCCCAGA GACGTCCGGG GGTGAGGCCG GCAGTGGGGA CGGGGGTTAC
1951 AAGCCCTTCC AGAGCCTCAC TCCTGGCTGC CCTGGGGCCC CGCCCCAGT
2001 CCCCGTCCCC CTGTTCACCT TCGGACTGGA CGCGGAGCCA CCTCATTGCC
2051 CGCAGGACTC CCCCCTCCCG GGCAGCTCCC CAGAGCCAGC GGGGAAGGCG
2101 CAGGACAGCC ACAAGACCCC GCCGGCCCCG GAGCAGGCCG CAGACCCCCT
2151 CCGGGACGAC CTGGCCAGCG GCATTGTCTA CTCAGCCCTC ACCTGCCACC
2201 TGTGTGGCCA CCTGAAACAG TGTCACGGCC AGGAGGAGGG AGGCGAGGCC
2251 CACCCCGTGG CCAGCCCCTG CTGCGGCTGC TGCCGTGGAG ACAGGTCCTC
2301 GCCGCTGGTG AGCCCTCTGA GGGCCCCGGA CCCCCTGCCA GGTGGGGTGC
2351 CCCTGGAGGC CAGCCTCTCT CCAGCCTCCC CGGCACCCTT GGCTGTCTCA
2401 GAGGAGGGCC CGCCCTCCCT GTGCTTCCAG CCTGCCCTGA GCCATGCTCA
```

FIG. 11A

```
2451  CAGCTCAAGC CAGACCCCCA AAAAGGTGGC CATGCTCTCC CCAGAGCCCA
2501  CGTGCACGAT GGCTTCCTAG GCGCGTGCCC GCTTGTCACT GCCGTCTTCG
2551  AGTGAGGGCT GGGCCTTAGC CCGGCCTGGG AAGTGCCTCC CCCGGAAGGC
2601  GGCTAGGCTG GAGGATTTGC AAAAGACTTG GAGAACCCTG CTATGAAGCT
2651  GGGAGGTGGT CTGACCTGGG GGTACAGAGA CTGGGCTCCA CCCCACCCCT
2701  CCCCCAGCTC CCAGCCCTGG CCTGGGGCTC GCCACAACCC AAGGGAGTGG
2751  AGGGCACGGG GGAGAGGCCC CTGCGGGATC GGGAGCTCCT TGGGGTGCCT
2801  CG
```

FIG. 11B

| | | |
|---|---|---|
| dog il4r | (1) | MGWLCSGLTFPVSCIVLWVASSGSVKVIHEPSCFSDYISTSVCQWKMDH |
| cat il4r | (1) | MGRLCSGLTFPVSCIVLWAAGSGSVKVLRAPTCFSDYFSTSVCQWNMDA |
| dog il4r | (51) | PTNCSAELRLSYQIDEMGSENHTCVPENREDSVCVCSMPIDDAVEADVYQ |
| cat il4r | (51) | PTNCSAELRLSYQLNFMGSENRTCVPENGEAACACSMIMDDFVEADVYQ |
| dog il4r | (101) | LDLIWAGQQLLWSGGSFQPSKHVKPRITPGNLTVHPNISHTWLLMWTNPYPTE |
| cat il4r | (101) | LHLIWAGTQLLWSGGSFKPSSHVKPRAPGNLTVHPNVSHIWLLRWSNPXPP |
| dog il4r | (151) | NHLHSELTYMVNSNDNDPEDFKVYNVTYMGPTLRLAASTIKSGASYSAR |
| cat il4r | (151) | NHLHAELTYMVNIISSEDDPTDSRIYNVTYMGPTLRVAASTITSGASYSAR |
| dog il4r | (201) | VRAWAQTYNSTWSDWSPSTRWLNYYEPWEQHLPLGVSISCLVILAICLSC |
| cat il4r | (201) | VRAWAQSYNSTWSEWSPSTKWLNHYFPWEQHLPLGVSISCLVILAVCLSC |
| dog il4r | (251) | YFSIIKIKKGMWDQIPNPAHSPLVALVIQDSQVSLWGKRSRGQEPAKCPH |
| cat il4r | (251) | YLSVIKIKKEMWDQIPNPAHSLVAIVIRDPQVSLWGKRSRGQEPAKCPH |
| dog il4r | (301) | WKTCLITKLLPCLLEHGLGREESPKTAKNGPLQGPGKPAWCPVEVSKTIL |
| cat il4r | (301) | WKTCLRKLLPCLLEHGMERKEDPSKITARNGPSQCSGKSAWCPVEVSKTIL |
| dog il4r | (351) | WPESISVVQCVELSEAPVDNEEEEE--VEEDKRSLCPSLEGGSGSFQEGRE |
| cat il4r | (351) | WPESISVVRCVELIEAPVESEEEEEEEDKGSFCPSPVNLEDSFQEGRE |
| dog il4r | (400) | GIVARLTESLFTDLLGGENGGECPQGLEESCLPPPSGSSVGAQMPWAQFPR |
| cat il4r | (401) | GIAARLTESLFMDLILGVEKGGFGPQGSIESWPPPSGSAGAQMPWAEFPG |

IL4 RECEPTOR ANTAGONISTS FOR HORSE, DOG AND CAT

CROSS-REFERENCE TO RELATED PATENT APPLICATIONS

The present application claims benefit of priority to U.S. Provisional Patent Application No. 60/475,220, filed May 30, 2003 and U.S. Provisional Patent Application No. 60/561,579, filed Apr. 12, 2004, each of which are incorporated by reference for any purpose.

BACKGROUND OF THE INVENTION

Interleukin-4 (IL4) is a cytokine produced by several cell types, including activated T cells, mast cells and basophils, which exhibits multiple functions in the immune system. See, e.g., Paul, W. E., *Blood* 77: 1859–70 (1991). IL4 is a B cell growth factor, enhances cell surface expression of high affinity IgE receptors on mast cells and low affinity IgE receptors (CD23) on B cells and mononuclear phagocytes, and promotes immunoglobulin isotype switching to IgE. See, e.g., Coffman, R. L., et al. *Adv Immunol* 54: 229–70 (1993); Conrad, et al. *J Immunol* 141:1091–7 (1988); Keegan, et al. *J Immunol* 142: 3868–74 (1989); Noelle, et al. *Proc Natl Acad Sci USA* 81:6149–53 (1984); Vercelli, et al. *J Exp Med* 167: 1406–16 (1988). The immunoregulatory role of IL4 in allergic diseases and activation of Th2 type responses has been well demonstrated in mice. See, e.g., Kopf, et al. *Nature* 362: 245–8 (1993); Lohoff, et al. *Int Arch Allergy Immunol* 115: 191–202 (1993). IL4 binds cell-surface, high-affinity receptors that are heterodimers, consisting of a specific α subunit and common γc subunit that is shared with IL2, IL7, IL9 and IL15. See, e.g., Idzerda, et al. *J Exp Med* 171: 861–73 (1990). IL4R is required for ligand binding at the receptor. See, e.g., Yin, et al., *J Biol Chem* 269: 26614–7 (1994). There is substantial evidence from genome-wide searches that IL4R is a good candidate gene for allergy and atopy in humans. See, e.g., CSGA, *Nat Genet* 15: 389–92 (1997); Ober, et al. *Hum Mol Genet* 7: 1393–8 (1998). Identification of polymorphisms of the functional domains of human IL4R is important due to the essential role of the IL4R complex in IL4 signalling pathway. See, e.g., Deichmann, et al, *Biochem Biophys Res Commun* 231: 696–7 (1997); Hershey, et al. *N Engl J Med* 337: 1720–5 1997). According to data deposited in dbSNP as of September 2002, the 9 non-synonomous coding region polymorphisms of human IL4R are, with only one exception, clustered within a 600 base pair segment of exon 12.

Soluble forms of the human IL4 receptor have been described for use as an antagonist of IL4 activity. See, e.g., U.S. Pat. Nos. 5,767,065 and 6,328,954. However, the art has not described the IL4 receptor of other animals.

Atopy and recurrent airway obstruction (RAO; previously referred to as COPD or heaves) are common diseases in the horse (*Equus caballus*). The immunologic basis of RAO has been firmly established (see, e.g., Beadle, et al. *Equine Veterinary Journal* 34: 389–394 (2002); Lavoie, et al. *American Journal of Respiratory & Critical Care Medicine* 164: 1410–1413 (2001); Marti, E. and Harwood, L. *Pferdeheilkunde* 18: 587 (2002)) and the disease etiology appears similar, but not identical, to asthma in humans. Similarly, allergic diseases occur in dogs and cats.

The present invention addresses this and other problems.

BRIEF SUMMARY OF THE INVENTION

The present invention provides isolated polynucleotides encoding an horse IL4 receptor. In some embodiments, the receptor comprises an amino acid sequence selected from the group consisting of SEQ ID NO:2; SEQ ID NO:2 comprising the change A464V; SEQ ID NO:2 comprising the change A554S; SEQ ID NO:2 comprising the change A559T; and SEQ ID NO:2 comprising the change A572V. In some embodiments, the nucleotide sequence is selected from the group consisting of: SEQ ID NO:1 and SEQ ID NO:1 comprising at least one of the following changes: C1208T, C1489T, G1758T, G1773A, G1808A, C1813T, C1829T, G1856A, T1937C, T2234C or C2333T.

The invention also provides isolated IL4 receptors comprising an amino acid sequence selected from the group consisting of: SEQ ID NO:2; SEQ ID NO:2 comprising the change A464V; SEQ ID NO:2 comprising the change A554S; SEQ ID NO:2 comprising the change A559T; and SEQ ID NO:2 comprising the change A572V.

The present invention also provides isolated polynucleotides encoding a horse, cat or dog soluble IL4 receptor. In some embodiments, the horse soluble IL4 receptor comprises SEQ ID NO:4. In some embodiments, the polynucleotide comprises SEQ ID NO:3. In some embodiments, the dog soluble IL4 receptor comprises SEQ ID NO:6. In some embodiments, the polynucleotide comprises SEQ ID NO:5. In some embodiments, the cat soluble IL4 receptor comprises SEQ ID NO:9. In some embodiments, the polynucleotide comprises SEQ ID NO:8.

The present invention also provides isolated soluble horse, dog or cat IL4 receptor polypeptides. In some embodiments, the horse IL4 receptor comprises SEQ ID NO:4. In some embodiments, the dog IL4 receptor comprises SEQ ID NO:6. In some embodiments, the cat IL4 receptor comprises SEQ ID NO:9.

The present invention also provides physiological compositions comprising the soluble horse, dog or cat IL4 receptor polypeptides, and a physiologically acceptable excipient.

The invention also provides methods for suppressing or inhibiting an IL4-mediated immune or inflammatory response in a horse, dog or cat. In some embodiments, the methods comprise administering to a horse, dog or cat an amount of a soluble horse, dog or cat IL4 receptor, respectively, effective to suppress or inhibit the IL4-mediated immune or inflammatory response.

In some embodiments, the immune or inflammatory response is an alloantigen-induced IL4-mediated immune or inflammatory response. In some embodiments, the IL4-mediated immune or inflammatory response is an allergic or asthmatic reaction. In some embodiments, the immune response results in a disease selected from the group consisting of atopy, recurrent airway obstruction, culicoides hypersensitivity, chronic recurrent urticaria, atopic dermatitis, and inflammatory airway disease.

In some embodiments, proliferation of lymphocytes is suppressed. In some embodiments, the immune response results in an IgE-induced condition. In some embodiments, the soluble horse IL4 receptor comprises SEQ ID NO:4.

The present invention also provides methods of identifying a horse that is predisposed for an IL4-mediated allergic condition. In some embodiments, the methods comprise providing a sample comprising a nucleic acid from the horse; and detecting the presence or absence of a polynucleotide in the sample, wherein the polynucleotide comprises a horse IL4 receptor haplotype CGGT, wherein C is position 1489 of SEQ ID NO:1, the first G is position 1758 of SEQ ID NO:1, the second G is position 1773 of SEQ ID NO:1 and the T is position 1813 of SEQ ID NO:1; thereby predicting the likelihood that the horse is predisposed for an allergic condition.

In some embodiments, the detecting comprises amplification of a polynucleotide from the sample. In some embodiments, the detecting step comprises a nucleic acid hybridization step. In some embodiments, the allergic condition is selected from the group consisting of recurrent airway obstruction, culicoides hypersensitivity, chronic recurrent urticaria, atopic dermatitis, and inflammatory airway disease. In some embodiments, the methods further comprise administering soluble IL4R to the horse predisposed for an allergic condition. In some embodiments, soluble IL4R is administered to the horse on a weekly basis.

DEFINITIONS

"Interleukin-4" and "IL4" is a T cell-derived cytokine involved in the regulation of immune and inflammatory responses. The biological activities of IL4 are mediated through binding to specific cell surface receptors, referred to as "Interleukin-4 receptors", "IL4 receptors" or simply "IL4R". "IL4 mediated" immune or inflammatory responses include all biological responses which are caused by the binding of IL4 to a native IL4 receptor (bound to a cell surface) or which may be inhibited or suppressed by preventing IL4 from binding to a native IL4 receptor. IL4 mediated biological responses include, for example, IL4 induced proliferation of antigen-primed B lymphocytes, expression of class II major histocompatibility complex molecules on resting B cells, secretion and expression of antibodies of the IgE and IgG1 isotype, and regulation of the expression of the low affinity Fc receptor for IgE (CD23) on lymphocytes and monocytes. Outside the B lymphocyte compartment, IL4 mediated biological responses include the proliferation of a variety of primary cells and in vitro cell lines, including factor-dependent T cell and mast cell lines, T lymphocytes, cytotoxic T cells, thymocytes, and connective tissue-type mast cells. Specific clinical conditions which may be mediated by IL4 include, for example, graft rejection, graft versus host disease, allergy, asthma and delayed-type hypersensitivity responses.

As used herein, the terms "IL4 receptor" or "IL4R" refer to proteins which bind interleukin-4 (IL4) molecules and, in their native configuration as intact plasma membrane proteins, play a role in transducing the biological signal provided by IL4 to a cell. Intact receptor proteins generally include an extracellular region which binds to a ligand, a hydrophobic transmembrane region which causes the protein to be immobilized within the plasma membrane lipid bilayer, and a cytoplasmic or intracellular region which interacts with cytoplasmic proteins and/or chemicals to deliver a biological signal to effector cells via a cascade of chemical reactions within the cytoplasm of the cell. The hydrophobic transmembrane region and a highly charged sequence of amino acids in the cytoplasmic region immediately following the transmembrane region cooperatively function to halt transport of the IL4 receptor across the plasma membrane. The horse transmembrane domain is represented at from about amino acids 223–255 of horse IL4R (SEQ ID NO:2), encoded by exon 9 (spanning from about nucleotides 766–865 of SEQ ID NO:1). In the dog IL4R sequence, the transmembrane region is from about amino acids 224–256 of SEQ ID NO:11 (encoded by nucleotides 677–773 of SEQ ID NO:7). In the cat IL4R sequence, the transmembrane region corresponds to amino acids 224–256 of SEQ ID NO:10 (encoded by nucleotides 731–830 of SEQ ID NO:8).

"Soluble IL4 receptor" or "sIL4-R" as used in the context of the present invention refers to a protein, or a substantially identical polypeptide, having an amino acid sequence comprising the extracellular region of the horse, dog or cat IL4 receptors. Examples of soluble polypeptides include those comprising the amino acid sequences substantially similar to SEQ ID NO:4 or SEQ ID NO:6 or SEQ ID NO:9. Because sIL4R proteins are devoid of a transmembrane region, they are secreted from the host cell in which they are produced. When administered in therapeutic formulations, sIL4R proteins circulate in the body and bind to circulating IL4 molecules, preventing interaction of IL4 with natural IL4 receptors and inhibiting transduction of IL4 mediated biological signals, such as immune or inflammatory responses. The ability of a polypeptide to inhibit IL4 signal transduction can be determined by transfecting cells with recombinant IL4 receptor DNAs to obtain recombinant receptor expression. The cells are then contacted with IL4 and the resulting metabolic effects examined. If an effect results which is attributable to the action of the ligand, then the recombinant receptor has signal transducing activity. Exemplary procedures for determining whether a polypeptide has signal transducing activity are disclosed by Idzerda, et al., *J Exp Med* 171: 861–73 (1990), Curtis et al., *Proc. Natl. Acad. Sci. USA* 86:3045 (1989), Prywes et al., *EMBO J.* 5:2179 (1986) and Chou et al., *J. Biol. Chem.* 262:1842 (1987). Soluble IL4 receptors occur naturally as splice variants that do not include the exon encoding the transmembrane domain. Soluble IL4 receptors can also be generated by deleting the transmembrane domain of IL4R (e.g., by truncating the protein, e.g., recombinantly or biochemically).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 amino acids or nucleotides in length, or more preferably over a region that is 75–100 amino acids or nucleotides in length. The present invention provides compositions and methods as described herein, involving sequences substantially similar to SEQ ID NOs:1, 2, 3, 4, 5, 6, 7, 8, 9, 10, or 11.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

One example of a useful algorithm is BLAST and BLAST 2.0 algorithms, which are described in Altschul et al. (1977) *Nuc. Acids Res.* 25:3389–3402, and Altschul et al. (1990) *J. Mol. Biol.* 215:403–410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); and Cassol et al. (1992); Rossolini et al., *Mol. Cell. Probes* 8:91–98 (1994)). The term nucleic acid is used interchangeably with gene, cDNA, and mRNA encoded by a gene.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins (i.e., antigens), wherein the amino acid residues are linked by covalent peptide bonds.

BRIEF DESCRIPTION OF THE DRAWINGS

FIGS. 1A and 1B illustrate a protein sequence lineup and polymorphisms of human (SEQ ID NO:14) and horse (SEQ ID NO:15) IL4R. The framed sequence shows portion of protein encoded by exon 12. Conserved residues are shaded. The extracellular WSXWS (SEQ ID NO:16 motif, the insulin/IL4 receptor motif and the 5 intracellular putative binding motifs with the central tyrosine labeled Y1 through Y5 are shown in reverse type. The equine IL4R splice variant replaces the sequence at position 223, marked with an asterisk, with "SP-stop." Arrows show positions of amino acid polymorphisms: up arrows show horse polymorphisms reported herein, and down arrows show human polymorphisms previously reported.

FIGS. 2A and 2B illustrate a comparison of horse IL4R (SEQ ID NO:2) and soluble IL4R (SEQ ID NO:4) amino acid sequences.

FIG. 4A illustrates the horse soluble IL4 receptor full length mRNA (SEQ ID NO:3). The coding region is underlined and the stop is in bold. FIG. 4B illustrates the predicted amino acid sequence of horse soluble IL4 receptor.

FIG. 5 illustrates the dog IL4 receptor partial mRNA sequence (SEQ ID NO:17) comprising the complete coding sequence underlined and the transmembrane region in bold.

FIG. 6 illustrates a naturally-occurring dog IL4R mRNA splice variant (SEQ ID NO:5) not encoding the transmembrane domain. The coding sequence is underlined.

FIG. 7 illustrates the naturally-occurring dog IL4R polypeptide (SEQ ID NO:11) comprising the transmembrane domain (in bold).

FIG. 8 illustrates the predicted amino acid sequence of the naturally-occurring dog soluble IL4 receptor (SEQ ID NO:6).

FIG. 9 illustrates the naturally-occurring cat IL4R polypeptide (SEQ ID NO:10) comprising the transmembrane domain (in bold).

FIG. 10 illustrates the amino acid sequence of a cat soluble IL4 receptor (SEQ ID NO:9).

FIGS. 11A and 11B illustrate the cat IL4 receptor partial mRNA sequence (SEQ ID NO:8) comprising the coding sequence (underlined) and sequence encoding the transmembrane domain (in bold).

Figure 12B:
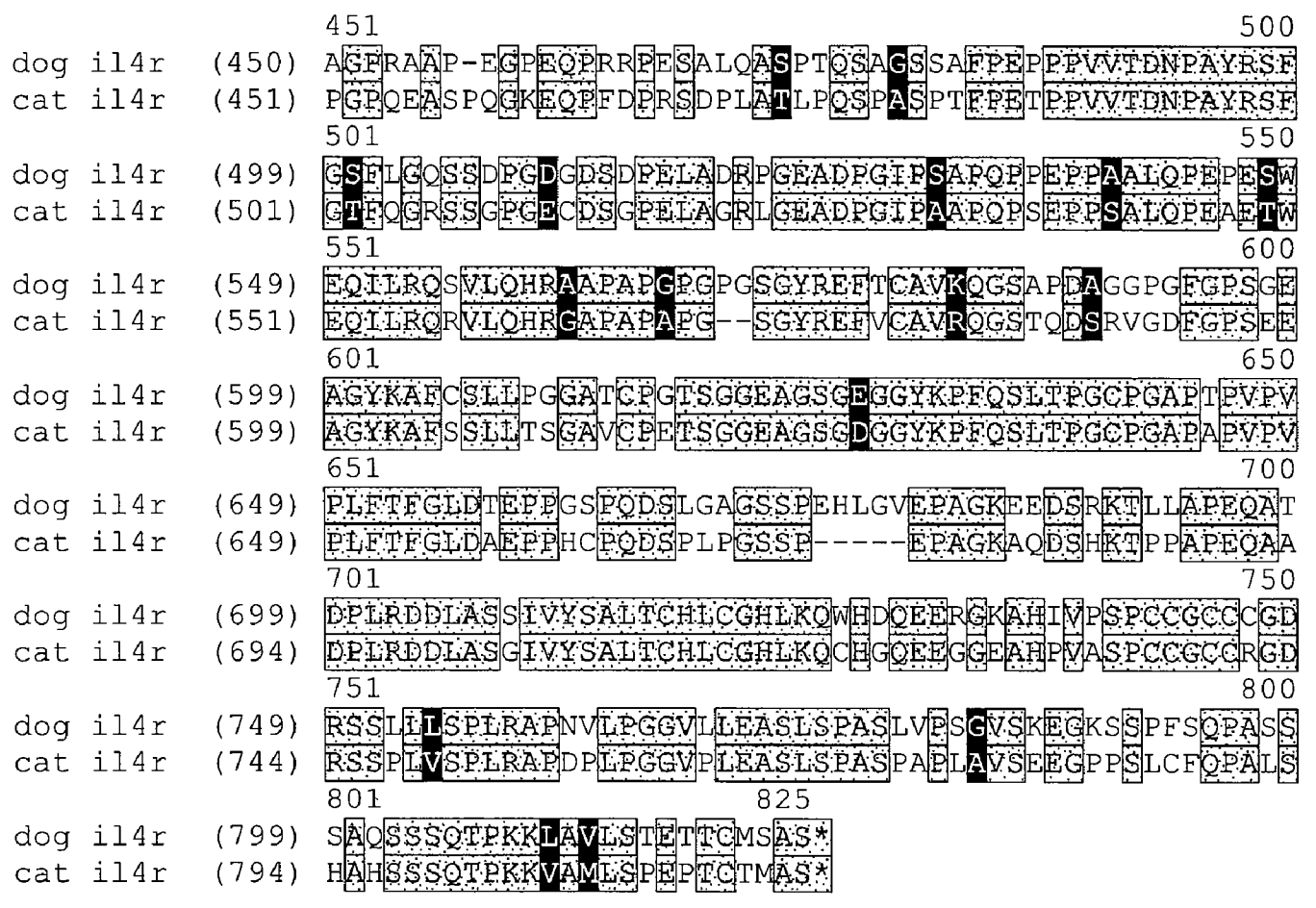

FIGS. 12A and 12B illustrate an alignment of the dog IL4R (SEQ ID NO:11) and the cat IL4R (SEQ ID NO:10) amino acid sequences.

FIG. 13 illustrates an alignment of the soluble dog IL4R (SEQ ID NO:6), the soluble horse IL4R (SEQ ID NO:4) and the soluble cat LL4R (SEQ ID NO:18) amino acid sequences.

DETAILED DESCRIPTION OF THE INVENTION

I. Introduction

Figure 1B:
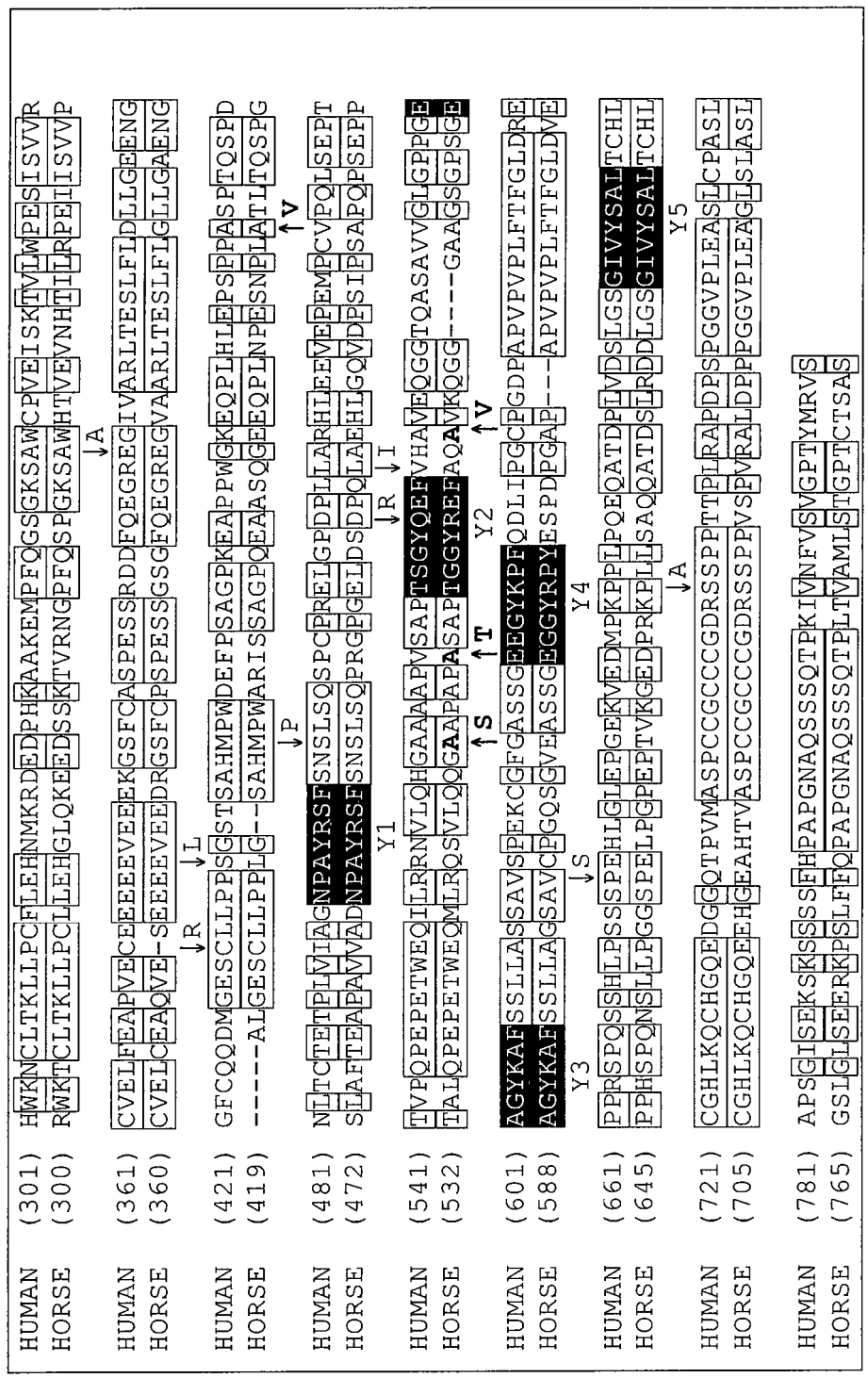

The present invention provides the discovery of horse, cat and dog IL4 receptor polypeptide and polynucleotide sequences. The invention also provides soluble dog, cat or horse IL4 receptors as well as splice variants encoding soluble receptors. The invention also provides methods of suppressing or inhibiting IL4-mediated immune or inflammatory responses by administering soluble dog, cat or horse IL4 receptor to a dog, cat or horse, respectively.

The invention also provides an analysis of horse IL4 SNPs and their use to predict predisposition of IL4-mediated disease.

II. Polypeptides of the Invention

The present invention provides full length and soluble fragments of the horse, dog and cat IL4 receptor. Exemplary horse full length IL4 receptor sequences include, e.g., those that encode SEQ ID NO:2 or SNPs thereof, e.g., SEQ ID NO:2, comprising the change A464V; SEQ ID NO:2 comprising the change A554S; SEQ ID NO:2 comprising the change A559T; and SEQ ID NO:2, comprising the change A572V. Exemplary polynucleotide sequences encoding such polypeptides include, e.g., SEQ ID NO:1 or those described in Table 2. Exemplary soluble horse IL4R polypeptides comprise SEQ ID NO:4 (e.g., encoded by SEQ ID NO:3).

Exemplary full-length (comprising the transmembrane domain) dog IL4R polypeptides include, e.g., SEQ ID NO:11. Polynucleotides encoding the dog IL4R, including the transmembrane domain may comprise, e.g., SEQ ID NO:7. Exemplary soluble dog IL4R polypeptides comprise, e.g., SEQ ID NO:6 (e.g., encoded by SEQ ID NO:5).

Exemplary full-length (comprising the transmembrane domain) cat IL4R polypeptides include, e.g., SEQ ID NO:10 (encoded by, e.g., SEQ ID NO:8). Exemplary soluble cat IL4R polypeptides comprise, e.g., SEQ ID NO:9.

Derivatives of horse, dog and cat IL4R within the scope of the invention also include various structural forms of the primary protein which retain biological activity. Due to the presence of ionizable amino and carboxyl groups, for example, an IL4R protein may be in the form of acidic or basic salts, or in neutral form. Individual amino acid residues may also be modified by oxidation or reduction.

The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to IL4R amino acid side chains or at the N- or C-termini. Other derivatives of IL4R within the scope of this invention include covalent or aggregative conjugates of IL4R or its fragments with other proteins or polypeptides, such as by synthesis in recombinant culture as N-terminal or C-terminal fusions. IL4R protein fusions can comprise peptides added to facilitate purification or identification of IL4R (e.g., poly-His). IL4R polypeptides of the invention can be altered as described in, e.g., U.S. Pat. No. 5,767,065.

IL4R derivatives may also be obtained by mutations of IL4R or its subunits. An IL4R mutant, as referred to herein, is a polypeptide homologous to a horse, cat or dog IL4R (as displayed herein) but which has an amino acid sequence different from native IL4R because of a deletion, insertion or substitution. Bioequivalent analogs of IL4R proteins may be constructed by, for example, making various substitutions of residues or sequences or deleting terminal or internal residues or sequences not needed for biological activity. For example, cysteine residues can be deleted or replaced with other amino acids to prevent formation of incorrect intramolecular disulfide bridges upon renaturation. Generally, substitutions should be made conservatively; i.e., the most preferred substitute amino acids are those having physicochemical characteristics resembling those of the residue to be replaced. Similarly, when a deletion or insertion strategy is adopted, the potential effect of the deletion or insertion on biological activity should be considered.

Soluble IL4R polypeptides may be constructed by deleting terminal or internal residues or sequences. For example, by deleting the transmembrane region and intracellular domain of horse, dog, or cat IL4R or substituting the domains with hydrophilic residue, soluble receptor can be generated. The resulting protein is a soluble IL4R molecule which may retain its ability to bind IL4. An exemplary naturally-occurring soluble horse IL4R sequence is displayed in FIG. 4B. An exemplary artificial soluble horse IL4R sequence is SEQ ID NO:12. An exemplary naturally-occurring soluble dog IL4R sequence is depicted in FIG. 8. An exemplary artificial soluble dog IL4R sequence is SEQ ID NO:13. An exemplary soluble cat IL4R sequence is displayed in FIG. 10 (SEQ ID NO:9.

III. Expression of Recombinant Horse, Cat or Dog IL4R

Nucleic acids encoding the IL4R polypeptides of the invention can be used for recombinant expression of the proteins. In these methods, the nucleic acids encoding the proteins of interest are introduced into suitable host cells, e.g., bacteria, yeast, insect cells, plant cells or animal cells (e.g., CHO cells, COS cells, etc.), followed by induction of the cells to produce large amounts of the protein. The invention relies on routine techniques in the field of recombinant genetics, well known to those of ordinary skill in the art. A basic text disclosing the general methods of use in this invention is Sambrook et al., *Molecular Cloning, A Laboratory Manual* (2nd ed. 1989).

Nucleic acids for use as diagnostic oligonucleotide probes or for the recombinant expression of proteins can be isolated using a number of techniques. For instance, polypeptide sequences of the invention can be used to design degenerate oligonucleotide probes to screen a cDNA library. Amino acid sequencing is performed and oligonucleotide probes are synthesized according to standard techniques as described, for instance, in Sambrook et al., supra. Alternatively, oligonucleotide probes useful for identification of desired genes can also be prepared from conserved regions of related genes in other species.

Alternatively, amplification techniques such as polymerase chain reaction technology (PCR) can be used to amplify nucleic acid sequences of the desired gene directly from mRNA, from cDNA, from genomic libraries or cDNA libraries. Polymerase chain reaction (PCR) or other in vitro amplification methods may also be useful, for example, to clone nucleic acid sequences that code for proteins to be expressed, to make nucleic acids to use as probes for detecting the presence of the mRNA in physiological samples, for nucleic acid sequencing, or for other purposes (for a general overview of PCR, see *PCR Protocols: A Guide to Methods and Applications*. (Innis et al., eds., 1990).

Standard transfection methods are used to produce prokaryotic, mammalian, yeast or insect cell lines which express large quantities of the desired polypeptide, which is then purified using standard techniques (see, e.g., Colley et al., *J. Biol. Chem.* 264:17619–17622, 1989; *Guide to Protein Purification*, supra).

The nucleotide sequences used to transfect the host cells can be modified to yield IL4R polypeptide variants. For example, the polypeptides can vary from the naturally-occurring sequence at the primary structure level by amino acid, insertions, substitutions, deletions, and the like. These modifications can be used in a number of combinations to produce the final modified protein chain.

The amino acid sequence variants can be prepared with various objectives in mind, including facilitating purification and preparation of the recombinant polypeptide. The modified polypeptides are also useful for modifying plasma half life, improving therapeutic efficacy, and lessening the severity or occurrence of side effects during therapeutic use. The amino acid sequence variants are usually predetermined variants not found in nature but exhibit the same immunogenic activity as naturally occurring protein. In general, modifications of the sequences encoding the polypeptides may be readily accomplished by a variety of well-known techniques, such as site-directed mutagenesis (see Gillman & Smith, *Gene* 8:81–97 (1979); Roberts et al., *Nature* 328:731–734 (1987)). One of ordinary skill will appreciate that the effect of many mutations is difficult to predict. Thus, most modifications are evaluated by routine screening in a suitable assay, for the desired characteristic.

The particular procedure used to introduce the genetic material into the host cell for expression of the polypeptide is not particularly critical. Any of the well known procedures for introducing foreign nucleotide sequences into host cells may be used. These include the use of calcium phosphate transfection, spheroplasts, electroporation, liposomes, microinjection, plasmid vectors, viral vectors and any of the other well known methods for introducing cloned genomic DNA, cDNA, synthetic DNA or other foreign genetic material into a host cell (see Sambrook et al., supra). It is only necessary that the particular procedure utilized be capable of successfully introducing at least one gene into the host cell which is capable of expressing the gene.

The particular vector used to transport the genetic information into the cell is also not particularly critical. Any of the conventional vectors used for expression of recombinant proteins in prokaryotic and eukaryotic cells may be used. Expression vectors for mammalian cells typically contain regulatory elements from eukaryotic viruses.

The expression vector typically contains a transcription unit or expression cassette that contains all the elements required for the expression of the polypeptide DNA in the host cells. A typical expression cassette contains a promoter operably linked to the DNA sequence encoding a polypeptide and signals required for efficient polyadenylation of the transcript. The term "operably linked" as used herein refers to linkage of a promoter upstream from a DNA sequence such that the promoter mediates transcription of the DNA sequence. The promoter is preferably positioned about the same distance from the heterologous transcription start site as it is from the transcription start site in its natural setting. As is known in the art, however, some variation in this distance can be accommodated without loss of promoter function.

IV. Purification of IL4 Receptors

Purified horse, cat or dog IL4 receptors or analogs are prepared by culturing suitable host/vector systems to express the recombinant translation products of the DNAs of the present invention, and purifying IL4 receptor from the culture media or cell extracts.

Following the growth of the recombinant cells and expression of the polypeptide, the culture medium is harvested for purification of the secreted protein. The media are typically clarified by centrifugation or filtration to remove cells and cell debris and the proteins are concentrated by adsorption to any suitable resin or by use of ammonium sulfate fractionation, polyethylene glycol precipitation, or by ultrafiltration. Other routine means known in the art may be equally suitable. Further purification of the polypeptide can be accomplished by standard techniques, for example, affinity chromatography, ion exchange chromatography, sizing chromatography, $His_6$ (SEQ ID NO:19) tagging and Ni-agarose chromatography (as described in Dobeli et at., *Mol. and Biochem. Parasit.* 41:259–268 (1990)), or other protein purification techniques to obtain homogeneity. The purified proteins are then used to produce pharmaceutical compositions, as described below.

Alternatively, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. For example, a suitable affinity matrix can comprise an IL4 or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups.

Finally, one or more reversed-phase high performance liquid chromatography (RP-HPLC) steps employing hydrophobic RP-HPLC media, e.g., silica gel having pendant methyl or other aliphatic groups, can be employed to further purify an IL4R composition. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant mammalian IL4R can be disrupted by any convenient method, including freeze-thaw cycling, sonication, mechanical disruption, or use of cell lysing agents.

Fermentation of yeast that express horse, cat or dog IL4R as a secreted protein greatly simplifies purification. Secreted recombinant protein resulting from a large-scale fermentation can be purified by methods analogous to those disclosed by Urdal et al., *J Chromatog.* 296:171 (1984).

V. Prediction of Horses Predisposed for IL4 Mediated Disease.

The present invention provides methods of identifying horses that are predisposed for IL4-medated or -triggered disease. The methods involve detection of an IL4R polynucleotide in a horse and then detecting the presence or absence of a particular sequence or sequences associated with the disease.

In some cases, the horse polynucleotide will be amplified and/or hybridized with a probe as is well known in the art.

IL4 mediated diseases whose predisposition can be predicted include, e.g., recurrent airway obstruction, atopy, culicoides hypersensitivity, atopic dermatitis, chronic recurrent urticaria, inflammatory airway disease among others.

Horses that can be analyzed using these methods include, e.g., Standardbreds, Thoroughbreds, Quarterhorses, Arabians, Appaloosas, Paints, Warmblood, or other horse breeds or mixed-breeds. For example, detection in breeds, such as Quarterhorses, of the IL4R haplotype corresponding to CGGT, wherein C is position 1489, the first G is position 1758, the second G is position 1773 and the T is position 1813 (wherein the positions refer to those in SEQ ID NO: 1), indicates a predisposition for recurrent airway obstruction.

VI. Administration of Soluble IL4 Receptor Compositions

The present invention provides compositions comprising a therapeutically effective amount of soluble horse, dog and cat IL4 receptor proteins, as well as methods of using such compositions. Methods of using such compositions include, e.g, methods of suppressing IL4-dependent immune responses in horse, dog and cat by administering an effective amount of soluble horse, dog or cat IL4 receptor protein, respectively.

For therapeutic use, purified soluble IL4 receptor protein is administered to an animal, e.g., a horse, dog or cat, for treatment in a manner appropriate to the indication. Thus, for example, soluble IL4 receptor protein compositions administered to suppress immune function can be given by injection, continuous infusion, sustained release from implants, or other suitable technique. Typically, a soluble horse, cat or dog IL4 receptor therapeutic agent will be administered in the form of a composition comprising purified protein in conjunction with physiologically acceptable carriers, excipients or diluents. Such carriers will be nontoxic to recipients at the dosages and concentrations employed. The preparation of such compositions can entail combining the IL4R with buffers, antioxidants such as ascorbic acid, low molecular weight (e.g., less than about 10 residues) polypeptides, proteins, amino acids, carbohydrates including glucose, sucrose or dextrins, chelating agents such as EDTA, glutathione and other stabilizers and excipients. Neutral buffered saline or saline mixed with serum albumin can be used. A composition of the invention can be formulated as a lyophilized product using appropriate excipient solutions (e.g., sucrose) as diluents.

Appropriate dosages can be determined in trials; generally, soluble IL4 receptor dosages of from about 1 ng/kg/day to about 10 mg/kg/day, more preferably from about 500 ng/kg/day to about 5 mg/kg/day, and most preferably from about 5 ug/kg/day to about 2 mg/kg/day, are appropriate for inducing a biological effect. The amount and frequency of administration will depend, of course, on such factors as the nature and severity of the indication being treated, the desired response, the condition of the patient, and so forth.

Soluble horse, dog or cat IL4R proteins can be administered for the purpose of inhibiting IL4 dependent responses, such as suppressing immune responses in a horse, dog or cat. A variety of diseases or conditions are caused by IL4 dependent immune responses as determined by the ability of sIL4R to inhibit the response. Soluble IL4R compositions may be used, for example, to treat recurrent airway obstruction, atopy or other IL4-mediated or -triggered disease. Soluble IL4R inhibits IL4 dependent B cell proliferation and isotype specific (IgE) secretions. sIL4R may therefore be used to suppress IgE antibody formation in the treatment of IgE-induced immediate hypersensitivity reactions, such as allergic rhinitis (common hay fever), bronchial asthma, atopic dermatitis and gastrointestinal food allergy. Other diseases/conditions that can be treated with sIL4R include, e.g., recurrent airway obstruction (COPD or Heaves), culicoides hypersensitivity, atopic dermatitis, chronic recurrent urticaria, inflammatory airway disease in horse, atopic dermatitis in dog and feline asthma in felines.

sIL4R compositions may also be used to regulate the function of T cells. Under some circumstances T cell growth and proliferation can be mediated by growth factors such as IL4. For example, sIL4R suppresses or inhibits T-cell dependent responses to alloantigen. A variety of diseases or conditions are caused by an immune response to alloantigen, including allograft rejection and graft-versus-host reaction. In alloantigen-induced immune responses, sIL4R suppresses lymphoproliferation and inflammation which result upon activation of T cells. sIL4R is therefore effective in the clinical treatment of, for example, rejection of allografts (such as skin, kidney, heart, lung liver and pancreas transplants), and graft-versus-host reactions in patients who have received bone marrow transplants.

EXAMPLES

Example 1

This example describes the isolation of the horse full-length and soluble IL4 receptor.

Materials and Methods

Cloning, Sequencing, and Mapping the Equine IL4R Gene

Using primers IL4R 284f5'-GACTACATCAGCATCTC-CAC-3' (SEQ ID NO:20) and IL4R 505r 5'-CTTGAAG-GAGCTGTTCCAC-3' (SEQ II) NO:21), a 250-bp fragment from equine mesenteric lymph node cDNA was PCR amplified. We then amplified the 5' region of the gene using SMART RACE PCR (BD Biosciences Clontech, Palo Alto, Calif.) and gene-specific reverse primers. The resulting 450 bp fragment was cloned using TOPO TA Cloning (Invitrogen, Carlsbad, Calif.). Three colonies of transformed bacteria were selected, cultured, and then plasmid-purified with a QIAprep Spin Miniprep (Qiagen, Valencia, Calif.). Each of the three plasmids was completely sequenced in both directions. The resulting 446 bp consensus sequence provided positions 1 to 446 of the published sequence.

An expressed sequence tag having strong identity to human IL4R was obtained from large-scale sequencing of an equine monocyte cDNA library. The clone was plasmid-purified and sequenced as described above. The resulting 1776 bp consensus sequence provided positions 1778 to 3553 of the published sequence and included a 3' poly-A signal.

Primers designed from the 3' end of the RACE clone and the 5' end of the monocyte clone were used to amplify a 1.6 kb fragment from equine alveolar macrophage cDNA. This PCR fragment was cloned and sequenced as described above. The resulting 1549 bp consensus sequence provided positions 385 to 1933 of the published sequence, thus completing the equine IL4R cDNA sequence.

Retention profile for IL4R was established by scoring for presence or absence of equine IL4R PCR product among the clones in the UCDAVIS somatic cell hybrid panel (Shiue, et al., *Anim Genet.* 30(1):1–9 (1999)) and the 5000rad TAMU equine radiation hybrid panel (Chowdhary, et al., *Mamm Genome.* 13(2):89–94 (2002)). Hybrid clone DNA was amplified with horse specific IL4R primers designed to produce a 370 bp fragment and analyzed after electrophoresis on 2% agarose gels. Statistical analysis for synteny and RH mapping were performed as previously described (Shiue, et al., *Anim Genet.* 30(1):1–9 (1999); Chowdhary, et al., *Mamm Genome.* 13(2):89–94 (2002)). Synteny groups were established as outlined by Chevalet et al., *Cytogenet Cell Genet.* 43(3–4):132–9 (1986) and the RH data was analyzed with RHMAP 3.0 (Boehnke et al., *Am J Hum Genet.* 49(6):1174–88 (1991)).

Determination of Exon Boundaries and Alternative Splice Variant

Exon boundaries in the equine IL4R gene were predicted by aligning the equine sequence with the human sequence, for which the genomic structure had been previously described. See, Kruse, et al. *Int Immunol* 11: 1965–70 (1999). Primers were designed to flank each putative exon boundary. Equine genomic DNA was used as the template in separate PCR reactions and the products were cloned and sequenced as described above to provide sequence spanning each exon-intron boundary.

Products were amplified by nested PCR out of the 3'-RACE cDNA library using the SMART® RACE (BD Biosciences Clontech, Palo Alto, Calif.) 3' universal and 3' nested universal primers and two nested gene-specific primers. (IL4R 580f 5' -AACATCTCCAAGGACGAC-3' (SEQ ID NO:22) and IL4R 619f 5' -ACAACGTGACCTACATG-GAC-3' (SEQ ID NO:23)).

Blood samples from sixty horses of various breeds were collected from four veterinary research centers in North America. The sample set was composed of 17 Standardbreds, 15 Thoroughbreds, 10 Quarterhorses, 4 Arabians, 3 Appaloosas, 2 Paints, 1 Warmblood, and 8 mixed-breed horses. DNA isolation from equine blood was performed with the QIAamp DNA Blood Mini Kit (Qiagen). PCR amplification was performed with Platinum Taq DNA Polymerase (Invitrogen) according to the manufacturer's protocol. Thermal cycling conditions were 95° C. for 2 mm; 35 cycles of 95° C. for 30 s, 61° C. for 30 s, 72° C. for 1 mm 30 s; and a final 72° C. extension for 10 minutes. The primers, AF (5'-AAGCTCCTGCCCTGTTTACTG-3'; SEQ ID NO:24) and CR (5'-GGACCGCAGCAACCAGAG-3'; SEQ ID NO:25), were designed to amplify 1.5 kb (almost all) of the translated region of exon 12. This PCR product was purified with QIAquick PCR Purification Kit (Qiagen) and subsequently used as the template in six separate cycle sequencing reactions, each using one of the primers AF, AR (5'-GCTGTGGGTCTGAGTCAAGC-3'; SEQ ID NO:26), BF (5'TCAACCCAGAGTCAAATCCTCTG-3'; SEQ ID NO:27), BR (5'-TCCTCTCCCTTCACCGTCG-3'; SEQ ID NO:28), CF (5'-CCTATGAGAGCCCCGACC-3'; SEQ ID NO:29), or CR. Cycle sequencing chemistry was either DYEnamic ET Terminator (Amersham Biosciences, Piscataway, N.J.) or ABI PRISM BigDye Terminators V 3.0 (Applied Biosystems, Foster City, Calif.). Cycle sequence reaction products were analyzed on either a BaseStation (MJ Research, South San Francisco, Calif.) or an ABI PRISM 3100 Genetic Analyzer (Applied Biosystems).

The 360 sequence files, six from each of the sixty horses, were scored, assembled, and manually examined with the Phred-Phrap-Consed trio of programs (Ewing, et al. *Genome Res* 8: 175–85 (1998)). The resulting sequence assemblies were then automatically analyzed for evidence of SNPs with the PolyPhred program (Nickerson, et al., *Nucleic Acids Res* 25: 2745–51 (1997)). We verified each SNP reported by PolyPhred by manually examining the corresponding sequence trace for each horse. DNA from the blood of a single donkey was isolated, amplified, cloned, and sequenced as described above to provide an inter-species comparative sequence of exon 12.

Results

A 3553 bp sequence representing the equine IL4R gene was submitted to the GenBank nucleotide sequence database and has been assigned accession number AY081138. Gap alignment of the equine sequence revealed 75% identity with the 3597 bp human sequence (NM_000418) and 62% identity with the 3583 bp murine sequence (M27959.1).

Analysis of data on the UCDAVIS panel showed statistical support for synteny of IL4R with two RAPDs, four microsatellites and two genes: G-10 950, T-17 850, ASB1, ASB37, 99AHT43, LEX41, equine glucoronidase, beta (GUSB) and elastin (ELN)—all of which have been previously mapped to ECA13 (Shiue Y et al., *Anim Genet.* 30(1):1–9 (1999); Caetan, et al., *Genome Res.* 9(12):1239–49 (1999)). RH2PT identified linkage of IL4R to three microsatellites and one gene on ECA 13: ASB37 (LOD 6.61), glucoronidase, beta (LOD 5.25), LEX041

(LOD 5.25) and VHL47 (LOD 5.25). These results effectively locate IL4R to ECA13 and demonstrate conservation of synteny of ELN, GUSB and IL4R across human, mouse and horse genomes.

The predicted sequence for equine IL4R precursor protein (accession number AAL87462) contained 809 amino acid residues (FIGS. 1A and 1B), compared with 825 for the human (NP_000409) and 810 for the murine (AAA39299.1) forms. Gap alignment of the equine sequence with the other species produced 67% identity & 72% similarity with the human form and 52% identity & 58% similarity with the murine form (BLOSUM62 scoring matrix). The extracellular (amino terminal) portion of the protein sequence exhibits all the features typical of type I cytokine receptors (Beckmann, et at. *Chem Immunol* 51: 107–34 (1992)): the cysteine residues with conserved spacing, the WSXWS (SEQ ID NO:16) motif (at aa 211–215, numbering from the first encoded residue of the equine protein), and the fibronectin type III domain (at aa 123–212). The cytosolic portion of the protein contains 5 conserved tyrosine residues, the first (Y1) occurs in an insulinIlL4 motif (Ryan, et at. *Immunity* 4: 123–32 (1996)), the second, third and fourth (Y2, Y3, Y4) occur at potential STAT6 docking sites ( ) and the fifth (Y5) occurs in a proposed immunoregulatory tyrosine-based inhibitory motif (ITIIM) (Daeron, et at. *Immunity* 3: 635–46 (1995)). In addition to the conserved tyrosines, there is a tyrosine residue at position +3 from Y4 in the equine sequence. See, FIGS. 1A and 1B.

We experimentally determined the positions of eight exon boundaries. These exon boundaries (Table 1) are in accord with the splicing scheme for humans reported previously by Kruse et al. (*Int Immunol* 11: 1965–70 (1999)), whose numbering scheme we have followed. Although we did not sequence the intron between exons 6 and 7, we assume this exon boundary also follows the human splicing scheme. Using nested PCR, we amplified and cloned a 462 bp PCR product from an equine monocyte SMART® RACE 3'-cDNA library (BD Biosciences Clontech, Palo Alto, Calif.). The first 147 bp of this sequence is identical to exon 7 of equine IL4R while the last 315 bp of this sequence is 100% identical to sequence contained in the 2.6 kb between exons 7 and 9. The existence of such a cDNA is strong evidence for an equine homologue to an alternatively spliced, soluble form of IL4R, previously reported in humans and mice. The full-length cDNA sequence for the alternative splice form was submitted to the GenBank nucleotide sequence database and has been assigned accession number AY289616.

TABLE 1

Exon-intron boundries of the equine IL4R gene

|  | Exon Size | Donor seq | SEQ ID NO: | Pos. | Intron 5' end | Intron Size | Intron 3' end | Acceptor seq | SEQ ID NO: |  |
|---|---|---|---|---|---|---|---|---|---|---|
| Exon 3 | 88 | CGGCAGGCTCTG | 30 | 168 | gtaagtcac | 1.6 kb | tctccccag | GGAGCGTTAAGG | 31 | Exon 4 |
| Exon 4 | 139 | CGAGTTCTCTGA | 32 | 307 | gtaagcctg | 1.6 kb | tgtctacag | CAACCTCACGTG | 33 | Exon 5 |
| Exon 5 | 152 | CCAGCCGGCACG | 34 | 459 | gtgagcggg | 1152 | tctctgcag | TGAAACCCAGGG | 35 | Exon 6 |
| Exon 6 | 149 | GACCCCACGGAC | 36 | 608 | unverified | 5-6 kb | unverified | TTCAAAATCTAC | 37 | Exon 7 |
| Exon 7 | 157 | CGTGGCATAACT | 38 | 765 | gtgagtatc | 715 | atttcccag | CCCCCTGAACTC | 39 | Exon 8 |
| Exon 8 | 315 | CTTTTGCAAT (A)n | 40 | 1080 | (tattgttat) | 1567 | cacttgcag | ACTACGAGCAGC | 41 | Exon 9 |
| Exon 9 | 100 | CAGCATCATCAA | 42 | 865 | gtgagtcct | 2.3 kb | cttttcag | GATTAAGAAAGA | 43 | Exon 10 |
| Exon 10 | 79 | CAGGATTCTCAG | 44 | 944 | gtaggagag | 1385 | gtgttttag | GTGTCACTGTGG | 45 | Exon 11 |
| Exon 11 | 50 | AGCCAAGTGCCC | 46 | 994 | gtacgtaca | 428 | cttttgcag | ACGCTGGAAGAC | 47 | Exon 12 |
| Exon 12 | 2559 | TCTTTCTCTC (A)n | 48 | 3553 |  |  |  |  |  |  |

"Pos" in Table 1 refers to the last position of the donor sequence (AY081138). Exon 8, shown shaded, is expressed only in soluble IL4R, in which a stop codon truncates the protein before expression of the transmembrane and intracellular domains contained in exons 9 through 12.

"Pos" in Table 1 refers to the last position of the donor sequence (AY081138). Exon 8, shown shaded, is expressed only in soluble IL4R, in which a stop codon truncates the protein before expression of the transmembrane and intracellular domains contained in exons 9 through 12.

The PolyPhred program requires high quality sequence data for automatic SNP detection. By directly sequencing PCR products from the 60 horses, we obtained data of sufficiently high quality between positions 1040 and 2520, corresponding to amino acids 315–807 and thus comprising about 97% of the translated region of exon 12. Within this surveyed region we discovered 11 SNPs, including 7 synonymous and 4 non-synonymous base changes. The population frequencies of these polymorphic alleles are presented in Table 2.

TABLE 2

SNP positions and frequencies

| Pos. | Allele frequencies (n = 120) | | | | Genotype frequencies (n = 60) | | | | | Effect |
|---|---|---|---|---|---|---|---|---|---|---|
| 1208 | C | 119 (0.99) | T | 1 (0.01) | CC | 59 (0.98) | CT | 1 (0.02) | TT 0 (0.00) | — |
| 1489 | C | 118 (0.98) | T | 2 (0.02) | CC | 59 (0.98) | CT | 0 (0.00) | TT 1 (0.02) | A464V |

TABLE 2-continued

SNP positions and frequencies

| Pos. | Allele frequencies (n = 120) | | | | Genotype frequencies (n = 60) | | | | | | Effect |
|---|---|---|---|---|---|---|---|---|---|---|---|
| 1758 | G 104 (0.87) | T 16 (0.13) | GG 49 (0.82) | GT  6 (0.10) | TT  5 (0.08) | A554S |
| 1773 | G  99 (0.82) | A 21 (0.18) | GG 44 (0.73) | GA 11 (0.18) | AA  5 (0.08) | A559T |
| 1808 | G 110 (0.92) | A 10 (0.08) | GG 54 (0.90) | GA  2 (0.03) | AA  4 (0.07) | — |
| 1813 | C  68 (0.57) | T 52 (0.43) | CC 28 (0.47) | CT 12 (0.20) | TT 20 (0.33) | A572V |
| 1829 | C 112 (0.93) | T  8 (0.07) | CC 55 (0.92) | CT  2 (0.03) | TT  3 (0.05) | — |
| 1856 | A  72 (0.60) | G 48 (0.40) | AA 28 (0.47) | AG 16 (0.27) | GG 16 (0.27) | — |
| 1937 | T  68 (0.57) | C 52 (0.43) | TT 26 (0.43) | TC 16 (0.27) | CC 18 (0.30) | — |
| 2234 | T 103 (0.86) | C 17 (0.14) | TT 48 (0.80) | TC  7 (0.12) | CC  5 (0.08) | — |
| 2333 | C 117 (0.98) | T  3 (0.02) | CC 57 (0.95) | CT  3 (0.05) | TT  0 (0.00) | — |

"Pos" in Table 2 refers to the position relative to the first nucleotide of Genbank sequence AY081138. The amino acid position is relative to the first residue of the precursor IL4R protein (i.e., including signal peptide.)

Discussion

This is the first report of the sequence and genomic organization of equine IL4R. When equine IL4R is compared to human and murine forms, we identify both conservation and divergence of structural organization. The protein contains functional domains in cytosolic portion that are important for cell growth, gene regulation and, potentially, negative feedback functions of the receptor (reviewed in Nelms, K., et al. *Annu Rev Immunol* 17: 701–38 (1999)). Five tyrosine-centered motifs are conserved across human, mouse, and rat. The juxtatyrosine sequence of each of these motifs appears to determine the nature of the signal cascade that follows. For example, the phosphotyrosine at Y1 activates IRS-1, while the phosphotyrosines at Y2, Y3 and Y4 activate STAT6. Equine IL4R exhibits significant conservation at the Y1, Y2, Y3 and Y5-containing motifs, while the Y4-containing motif replaces a phenylalanine with a tyrosine residue 3 amino acids downstream from the central tyrosine. This F621Y substitution may change the signaling cascade specificity at this site. Also, it is interesting to note that the equine IL4R does not conform to the equal spacing of 27 amino acids between Y2–Y3 and Y3–Y4 observed by Ryan et al., *Immunol* 161: 1811–21 (1998). The predicted horse protein has only 23 residues between Y2–Y3 and this is the first evolutionary variation in this region reported to date.

A soluble form of IL4R, produced by alternative splicing, has been described in both humans and mice (Kruse, S., et al., *Int Immunol* 11: 1965–70 (1999); Mosley, et al. *Cell* 59: 335–48 (1989)). In both of these species, the soluble form is due to the presence of a stop codon early in exon 8, which is not part of the mRNA for the membrane-bound form. Both of these studies have demonstrated that the stop codon effectively truncates the IL4R protein just before the transmembrane region, thus producing a soluble receptor that retains its high binding affinity for IL4. In the horse, we have found very strong evidence for the existence of such a splice variant. The splicing scheme presented herein (FIGS. 1A and 1B) predicts that exon 8 encodes one amino acid followed by a stop codon, which is very similar to the schemes reported for the mouse and human form.

Previous studies of the human IL4R gene have described numerous polymorphisms, some of which alter the function of IL4R and some of which appear to be significantly associated with atopy. Almost all of the coding region, non-synonymous SNPs reported in humans are found in exon 12. Hershey, et al., *N Engl J Med* 337: 1720–5 (1997) reported that a SNP at nucleotide 1902 (Q576R, though sometimes referred to under a different numbering scheme as R551) was significantly associated with atopy in their sample population. Furthermore, they described enhanced signaling of the receptor protein due to a change in the binding specificity of the tyrosine residue at position 575. This tyrosine residue (Y2) is conserved between species, and occurs at position 566 in the equine IL4R protein sequence. It is interesting to note that the equine sequence contains a fixed arginine at position 567, making the sequence of the equine Y2-containing motif identical to this gain-of-function allele in the human. Furthermore, the three common, non-synonymous SNPs described in this study alter the equine protein sequence at amino acid positions −12, −7 and +6 from Y2.

Example 2

This example demonstrates that horse IL4R SNPs are associated with disease.

Figure 3:
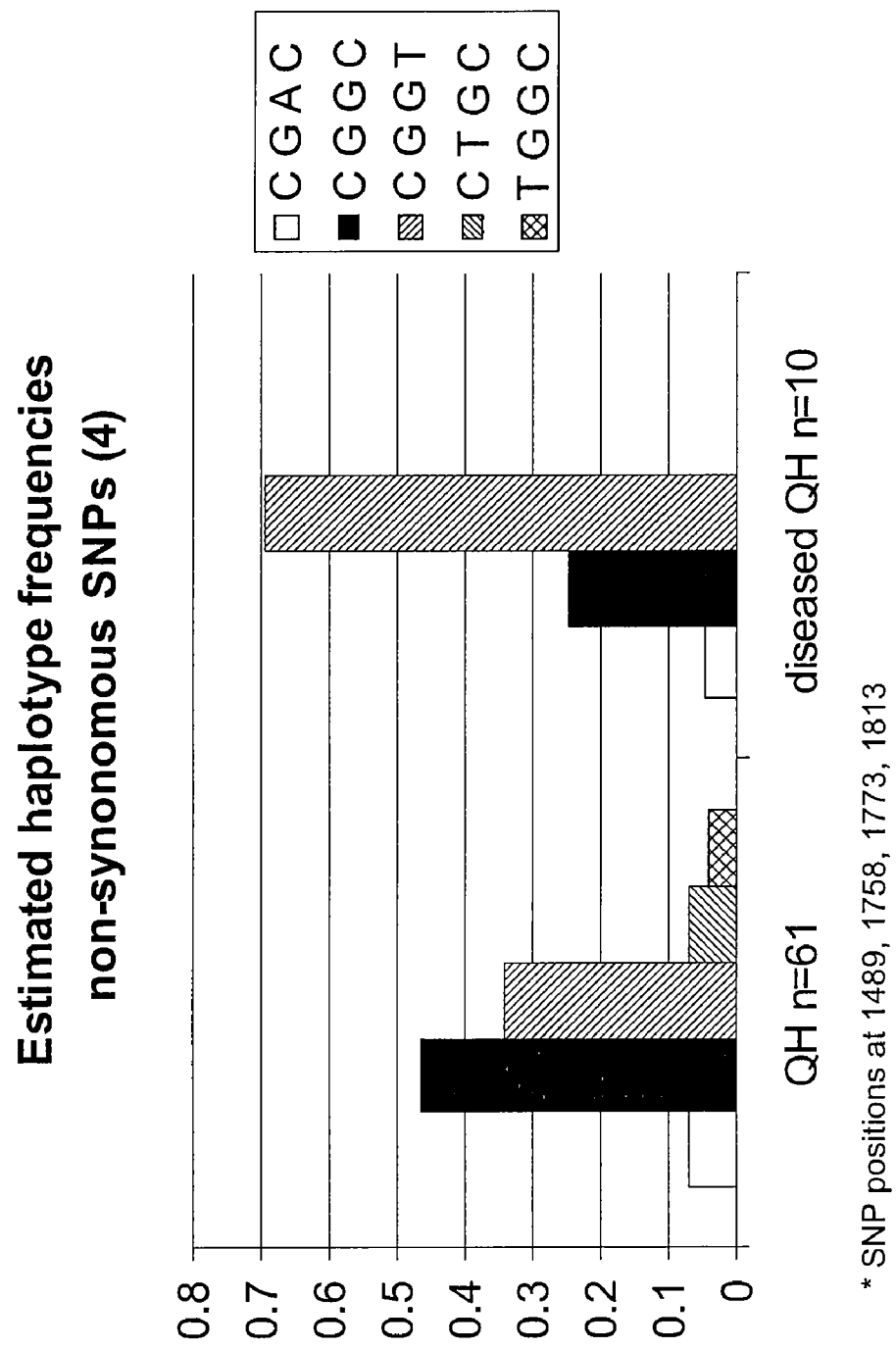
FIG. 3 illustrates the correlation of various SNP haplotypes with the occurrence of recurrent airway obstruction (RAO).

We identified 11 SNP's, 7 synonymous and 4 non-synonymous. When we looked at normal vs. diseased horses (those with well-characterized Recurrent Airway Obstruction (RAO)) we found no association with individual SNP or with haplotype. We did however find that there are breed specific haplotypes for IL4R in the horse. We have developed a data set of Quarterhorses (n=61). FIG. 3 displays the frequencies of 5 different haplotypes, representing the combinations of the 4 non-synonymous SNP's, in Quarterhorses and diseased Quarterhorses. This evidence demonstrates an association of one of these haplotypes, CGGT (where position 1489 is C, position 1758 is G, position 1773 is G and position 1813 is T), with RAO in Quarterhorses.

Example 3

This example provides the isolation of IL4R polynucleotides from dog and cat.

IL4R gene sequences from dog and cat were determined. FIG. 5 depicts the dog IL4R mRNA, with the coding sequence of the mRNA underlined. As illustrated in FIG. 5 in bold, exon 9 represents the exon encoding the transmembrane domain of the dog IL4 receptor. The predicted amino acid sequence encoded by the mRNA is displayed in FIG. 7.

Figure 13:
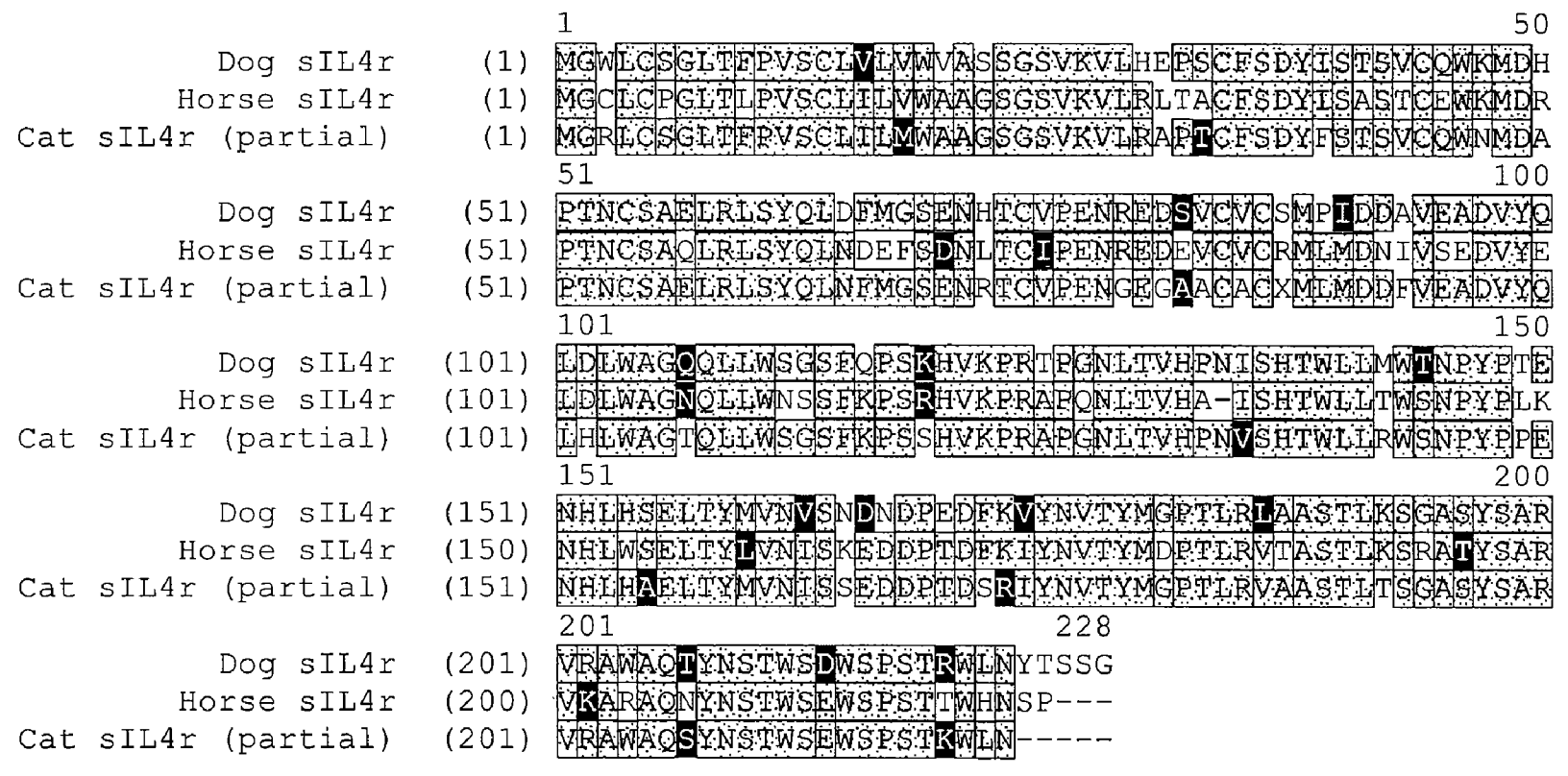

FIG. 6 depicts an alternative splice product of the dog IL4R gene lacking exon 9, thereby encoding a naturally-occurring soluble receptor. The predicted amino acid sequence of the soluble receptor is depicted in SEQ ID NO:8. FIG. 13 illustrates an alignment of the dog IL4R, the soluble dog IL4R, soluble cat IL4R, and the soluble horse IL4R amino acid sequences.

The cat IL4R gene sequence and mRNA sequence was also determined. FIGS. 11A and 11B depict a cat mRNA sequence with the coding region underlined and the transmembrane domain in bold. This mRNA encodes a cat IL4R polypeptide comprise in a transmembrane domain (FIG. 9). A predicted soluble cat IL4R sequence (representing most of the naturally-occurring soluble cat IL4R sequence) is depicted in FIG. 10 (SEQ ID NO:9).

All publications and patent applications cited in this specification are herein incorporated by reference as if each individual publication or patent application were specifically and individually indicated to be incorporated by reference. U.S. Provisional Patent Application No. 60/475,220, filed May 30, 2003 is incorporated by reference in its entirety for all purposes.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. An isolated soluble IL-4 receptor polypeptide comprising a polypeptide having at least 70% amino acid sequence identity to the polypeptide of SEQ ID NO:4, wherein said isolated soluble IL4 receptor polypeptide binds IL4.

2. The isolated soluble IL4 receptor polypeptide of claim 1 comprising a polypeptide having at least 95% amino acid sequence identity to the polypeptide of SEQ ID NO:4.

3. A composition comprising the soluble IL4 receptor polypeptide of claim 1, and a physiologically acceptable excipient.

4. The composition of claim 3, wherein the soluble IL4 receptor polypeptide comprises a polypeptide having at least 95% amino acid sequence identity to the polyeptide of SEQ ID NO:4.

5. The isolated soluble IL4 receptor of claim 1, wherein the IL4 receptor comprises SEQ ID NO:4.

6. An isolated IL4 receptor comprising the amino acid sequence selected from the group consisting of:
   SEQ ID NO:2;
   SEQ ID NO:2, except that the sequence includes the mutation A464V;
   SEQ ID NO:2, except that the sequence includes the mutation A554S;
   SEQ ID NO:2, except that the sequence includes the mutation A559T; and
   SEQ ID NO:2, except that the sequence includes the mutation A572 V.

* * * * *

SEQUENCE LISTING

<160> NUMBER OF SEQ ID NOS: 48

<210> SEQ ID NO 1
<211> LENGTH: 3553
<212> TYPE: DNA
<213> ORGANISM: Equus caballus
<220> FEATURE:
<223> OTHER INFORMATION: equine (horse) interleukin-4 (IL4) receptor (IL4R) cDNA

<400> SEQUENCE: 1

```
gggcgctgcc gagcctggct gccctggatc ccgcacttcc cgctcgggcg ctggacggcg      60
aatgggccag gggcgcgcag gtgcagtagg gtctcccaat ggggtgcctt tgccccgggc     120
tcacgctccc tgtgagctgc ctgatcctgg tgtgggcggc aggctctggg agcgttaagg     180
tcctgcgtct caccgcctgc ttctccgact acatcagcgc ctccacctgt gagtggaaga     240
tggaccgtcc caccaactgc agtgcccagc tccgtctgtc ctaccagctg aacgacgagt     300
tctctgacaa cctcacgtgt atccccgaga acagagaaga tgaagtgtgc gtgtgccgta     360
tgctgatgga caacatcgtc agcgaggacg tctatgagct ggacctgtgg gctgggaacc     420
aactgctgtg aacagctcc ttcaagccca gccggcacgt gaaacccagg gcccctcaaa     480
acctcacggt tcacgccatc tcccacacgt ggctgctgac gtggagcaac ccgtacccct     540
tgaagaatca cctgtggtct gagcttacct acctggtcaa catctccaag gaggacgacc     600
ccacggactt caaaatctac aacgtgacct acatggaccc caccctccgc gtcacagcca     660
gcaccctgaa gtccagggct acgtacagcg cacgggtgaa ggccagggct cagaactaca     720
acagcacctg gagtgagtgg agcccagca ccacgtggca taactactac gagcagccct     780
tggagcagcc cctcccgctt ggtgtcagca tctcctgcgt tgtcatcctg gccatctgcc     840
tgtcctgcta tttcagcatc atcaagatta agaaagaatg gtgggaccag attcccaacc     900
cagcgcacag ccccctcgtg gctatcgtcc tccaggattc tcaggtgtca ctgtggggga     960
agcagtcccg aggccaggag ccagccaagt gcccacgctg gaagacttgt cttaccaagc    1020 tcctgcctctg tttactggag catggcctgc aaaaggagga ggattcctcc aagactgtca    1080
gaaatgggcc tttccagagt cctggaaaat cagcatggca cactgtggag gtcaaccaca    1140
cgatcctccg gccagagatc atcagcgtgg tgccgtgtgt ggagctgtgt gaggcccagg    1200
tggagagcga ggaggaggaa gtggaggaag atagagggag cttctgcccg tcgcctgaga    1260
gcagcgggag cggcttccag gaaggcaggg agggcgtcgc ggcccggctg acagagagcc    1320
tgttcctggg cctcctcggg gctgagaatg gggccttggg ggagtcatgc cttcttcccc    1380 cttttaggaag tgctcacatg ccctgggcca ggatctcaag tgcagggccc caggaggcag    1440
```

```
cgtcccaggg tgaggagcag cctctcaacc cagagtcaaa tcctctggcc actctgaccc    1500
agagcccagg cagcctggct ttcacagagg cgcctgctgt ggttgcagac aaccccgcct    1560
accgcagctt cagcaactcc ctgagccagc cccgaggtcc tggagagctt gactcagacc    1620
cacagctggc cgaacacctg gccaagtgg accccagcat cccctccgcc ccccagccct     1680
ctgaaccacc cactgcactc cagcctgaac cagaaacctg ggagcagatg ctccgccaga    1740
gtgtcctcca gcagggggca gccccagccc ccgcctcggc ccccactggc ggctaccggg    1800
agtttgcgca ggtggtgaag cagggtgcg gggcggcggg ctccggccct tctggggagg     1860
ctgggtacaa ggccttctcc agcctgctcg ctggcagtgc cgtctgccca gggcaatctg    1920
gggttgaggc cagcagtggg gagggggct acaggcccta tgagagcccc gaccctggag      1980
cccctgcccc ggtccccgtc ccctgttca cctttggact ggatgtggag ccacctcaca     2040
gccctcagaa ctccctcctg ccaggcggct cccagagct ccctggccca gagccgacgg     2100
tgaagggaga ggacccacgg aagcccctgc tttccgcaca gcaggccaca gactccctca    2160
gggacgacct gggcagcggc attgtctact cggccctcac ctgccacctt tgtggccacc    2220
tgaagcagtg tcatggccag gaggagcatg gcgaggccca cactgtggcc agccctgct     2280 gtggctgctg ttgtggggac aggtcctccc ccccagtgag ccccgtgagg gccctggacc    2340
ccccgccagg tggggttccc ctggaggcgg gcctctctct tgcctccctg ggatccttgg    2400
ggctctctga ggagcgcaaa ccctcccctct tcttccagcc tgctcccggc aatgctcaga    2460
gctcgagcca gaccccctc acggtggcca tgctctccac agggcccaca tgcacgagcg     2520
cttcctaggg gcgtgccctc tggttgctgc ggtccacagg tgaggaccgg gtcttcgaaa    2580
tgcctccccc cacattttgg ggcagccagg ctggcagact tctgaaagac tcagagaacc    2640
ctggtaggaa gctgtgaggt tgtccaacct ggggctacag agactggacc cccttgctcc    2700
cagccgtggc ccaagctccc cccatcccac gggagtggag cctgcaggggc agccatgccc   2760 acggcaggca cctgcgggca tcgggaggtc cctgggcagc tgagcttgtg aacgagccgt    2820
tggccgcttc gttggtgcac agcttctcca gcatgctgtc cctgtcacgc ctgcccaagg    2880
cttgttttgt ccacctaatc tctctgttac ccgagtctga cccagtcctg ggttagctgc    2940
cgccatatca ctggattgga tgctgagcct agaaactgat caagctcatg ggggaatgac    3000
ttaggaggcc ccaggaaatt caagggaagt cggggtccag gaggatagga tttgcctaga    3060
gaggcccgtt ccttcaacag agcttcatct agctggcacc agaggcagga ttgcacctgt    3120
ggtgggtgct tagccaagtc ggggtcacag agaaggacat gagaaattgt gattagccgg    3180
tagtgacagt ttgctgtcag gtccccccac aactgtaggc ctgggcctcc tcttaggcat    3240
gggatcccca gagtggacct gcccagctac ccagggccag tttgtgcacc catggagagc    3300
gttgctggca gccatagaga ccagagggag tgggtcacag cccatgaccc agccgaatgg    3360
ggcattccag acagctgacc cggcacgttt tgcctgcaca tggctcagac cttgggtcga    3420
gtaacgcttg tttgtgtgta tctcaaagat tattttatct cctggtattt gtgtttgctg    3480
aggacggtgg aatgggggg tctggagtct tgtatgaata aagattcttt ctctcaaaaa     3540
aaaaaaaaaa aaa                                                       3553

<210> SEQ ID NO 2
<211> LENGTH: 809
<212> TYPE: PRT
<213> ORGANISM: Equus caballus
<220> FEATURE:
```

<223> OTHER INFORMATION: equine (horse) interleukin-4 (IL4) receptor (IL4R)

<400> SEQUENCE: 2

```
Met Gly Cys Leu Cys Pro Gly Leu Thr Leu Pro Val Ser Cys Leu Ile
 1               5                  10                  15

Leu Val Trp Ala Ala Gly Ser Gly Ser Val Lys Val Leu Arg Leu Thr
             20                  25                  30

Ala Cys Phe Ser Asp Tyr Ile Ser Ala Ser Thr Cys Glu Trp Lys Met
         35                  40                  45

Asp Arg Pro Thr Asn Cys Ser Ala Gln Leu Arg Leu Ser Tyr Gln Leu
     50                  55                  60

Asn Asp Glu Phe Ser Asp Asn Leu Thr Cys Ile Pro Glu Asn Arg Glu
 65                  70                  75                  80

Asp Glu Val Cys Val Cys Arg Met Leu Met Asp Asn Ile Val Ser Glu
                 85                  90                  95

Asp Val Tyr Glu Leu Asp Leu Trp Ala Gly Asn Gln Leu Leu Trp Asn
            100                 105                 110

Ser Ser Phe Lys Pro Ser Arg His Val Lys Pro Arg Ala Pro Gln Asn
        115                 120                 125

Leu Thr Val His Ala Ile Ser His Thr Trp Leu Leu Thr Trp Ser Asn
130                 135                 140

Pro Tyr Pro Leu Lys Asn His Leu Trp Ser Glu Leu Thr Tyr Leu Val
145                 150                 155                 160

Asn Ile Ser Lys Glu Asp Asp Pro Thr Asp Phe Lys Ile Tyr Asn Val
                165                 170                 175

Thr Tyr Met Asp Pro Thr Leu Arg Val Thr Ala Ser Thr Leu Lys Ser
            180                 185                 190

Arg Ala Thr Tyr Ser Ala Arg Val Lys Ala Arg Ala Gln Asn Tyr Asn
        195                 200                 205

Ser Thr Trp Ser Glu Trp Ser Pro Ser Thr Thr Trp His Asn Tyr Tyr
    210                 215                 220

Glu Gln Pro Leu Glu Gln Arg Leu Pro Leu Gly Val Ser Ile Ser Cys
225                 230                 235                 240

Val Val Ile Leu Ala Ile Cys Leu Ser Cys Tyr Phe Ser Ile Ile Lys
                245                 250                 255

Ile Lys Lys Glu Trp Trp Asp Gln Ile Pro Asn Pro Ala His Ser Pro
            260                 265                 270

Leu Val Ala Ile Val Leu Gln Asp Ser Gln Val Ser Leu Trp Gly Lys
        275                 280                 285

Gln Ser Arg Gly Gln Glu Pro Ala Lys Cys Pro Arg Trp Lys Thr Cys
    290                 295                 300

Leu Thr Lys Leu Leu Pro Cys Leu Leu Glu His Gly Leu Gln Lys Glu
305                 310                 315                 320

Glu Asp Ser Ser Lys Thr Val Arg Asn Gly Pro Phe Gln Ser Pro Gly
                325                 330                 335

Lys Ser Ala Trp His Thr Val Glu Val Asn His Thr Ile Leu Arg Pro
            340                 345                 350

Glu Ile Ile Ser Val Val Pro Cys Val Glu Leu Cys Glu Ala Gln Val
        355                 360                 365

Glu Ser Glu Glu Glu Val Glu Asp Arg Gly Ser Phe Cys Pro
    370                 375                 380

Ser Pro Glu Ser Ser Gly Ser Gly Phe Gln Glu Gly Arg Glu Gly Val
385                 390                 395                 400
```

```
Ala Ala Arg Leu Thr Glu Ser Leu Phe Leu Gly Leu Gly Ala Glu
            405                 410                 415

Asn Gly Ala Leu Gly Glu Ser Cys Leu Leu Pro Pro Leu Gly Ser Ala
            420                 425                 430

His Met Pro Trp Ala Arg Ile Ser Ser Ala Gly Pro Gln Glu Ala Ala
            435                 440                 445

Ser Gln Gly Glu Glu Gln Pro Leu Asn Pro Glu Ser Asn Pro Leu Ala
    450                 455                 460

Thr Leu Thr Gln Ser Pro Gly Ser Leu Ala Phe Thr Glu Ala Pro Ala
465                 470                 475                 480

Val Val Ala Asp Asn Pro Ala Tyr Arg Ser Phe Ser Asn Ser Leu Ser
            485                 490                 495

Gln Pro Arg Gly Pro Gly Glu Leu Asp Ser Asp Pro Gln Leu Ala Glu
            500                 505                 510

His Leu Gly Gln Val Asp Pro Ser Ile Pro Ser Ala Pro Gln Pro Ser
            515                 520                 525

Glu Pro Pro Thr Ala Leu Gln Pro Glu Pro Glu Thr Trp Glu Gln Met
    530                 535                 540

Leu Arg Gln Ser Val Leu Gln Gln Gly Ala Ala Pro Ala Pro Ala Ser
545                 550                 555                 560

Ala Pro Thr Gly Gly Tyr Arg Glu Phe Ala Gln Val Val Lys Gln Gly
            565                 570                 575

Gly Gly Ala Ala Gly Ser Gly Pro Ser Gly Glu Ala Gly Tyr Lys Ala
            580                 585                 590

Phe Ser Ser Leu Leu Ala Gly Ser Ala Val Cys Pro Gly Gln Ser Gly
            595                 600                 605

Val Glu Ala Ser Ser Gly Glu Gly Tyr Arg Pro Tyr Glu Ser Pro
            610                 615                 620

Asp Pro Gly Ala Pro Ala Pro Val Pro Val Pro Leu Phe Thr Phe Gly
625                 630                 635                 640

Leu Asp Val Glu Pro Pro His Ser Pro Gln Asn Ser Leu Leu Pro Gly
            645                 650                 655

Gly Ser Pro Glu Leu Pro Gly Pro Glu Pro Thr Val Lys Gly Glu Asp
            660                 665                 670

Pro Arg Lys Pro Leu Leu Ser Ala Gln Gln Ala Thr Asp Ser Leu Arg
            675                 680                 685

Asp Asp Leu Gly Ser Gly Ile Val Tyr Ser Ala Leu Thr Cys His Leu
            690                 695                 700

Cys Gly His Leu Lys Gln Cys His Gly Gln Glu Glu His Gly Glu Ala
705                 710                 715                 720

His Thr Val Ala Ser Pro Cys Cys Gly Cys Cys Gly Asp Arg Ser
            725                 730                 735

Ser Pro Pro Val Ser Pro Val Arg Ala Leu Asp Pro Pro Gly Gly
            740                 745                 750

Val Pro Leu Glu Ala Gly Leu Ser Leu Ala Ser Leu Gly Ser Leu Gly
            755                 760                 765

Leu Ser Glu Glu Arg Lys Pro Ser Leu Phe Phe Gln Pro Ala Pro Gly
    770                 775                 780

Asn Ala Gln Ser Ser Ser Gln Thr Pro Leu Thr Val Ala Met Leu Ser
785                 790                 795                 800

Thr Gly Pro Thr Cys Thr Ser Ala Ser
            805
```

<210> SEQ ID NO 3
<211> LENGTH: 1080
<212> TYPE: DNA
<213> ORGANISM: Equus caballus
<220> FEATURE:
<223> OTHER INFORMATION: equine (horse) interleukin-4 (IL4) receptor
    (IL4R) alternate splice product, horse soluble IL4R full length
    mRNA

<400> SEQUENCE: 3

```
gggcgctgcc gagcctggct gccctggatc ccgcacttcc cgctcgggcg ctggacggcg     60
aatgggccag gggcgcgcag gtgcagtagg gtctcccaat ggggtgcctt tgccccgggc    120
tcacgctccc tgtgagctgc ctgatcctgg tgtgggcggc aggctctggg agcgttaagg    180
tcctgcgtct caccgcctgc ttctccgact acatcagcgc ctccacctgt gagtggaaga    240
tggaccgtcc caccaactgc agtgcccagc tccgtctgtc ctaccagctg aacgacgagt    300
tctctgacaa cctcacgtgt atccccgaga acagagaaga tgaagtgtgc gtgtgccgta    360
tgctgatgga caacatcgtc agcgaggacg tctatgagct ggacctgtgg gctgggaacc    420
aactgctgtg gaacagctcc ttcaagccca gccggcacgt gaaacccagg gcccctcaaa    480
acctcacggt tcacgccatc tcccacacgt ggctgctgac gtggagcaac ccgtacccct    540
tgaagaatca cctgtggtct gagcttacct acctggtcaa catctccaag gaggacgacc    600
ccacggactt caaaatctac aacgtgacct acatggaccc caccctccgc gtcacagcca    660
gcaccctgaa gtccagggct acgtacgcgc acgggtgaa ggccagggct cagaactaca    720
acagcacctg gagtgagtgg agccccagca ccacgtggca taactccccc tgaactctat    780
ctgcagcctt gctggaagtc tgtggacccc gagttaagat ttctgctctg ggcactgcca    840
tcatctgcat ccaggcagca gaaggggaa ggagagcagg gagaccaaac ccgcttctta    900
aaagcctcag cccagaagtg acgcacgtca cttcctctca ggttctgttg gtgaaattgg    960
tcacgtggct acatgtagct gcaagggatt ctgggaaatg tagtccctca cttggtagct   1020
gcacccgccc cccccagtaa ctctttacag atctatcaca catggctttt gcaataaaaa   1080
```

<210> SEQ ID NO 4
<211> LENGTH: 224
<212> TYPE: PRT
<213> ORGANISM: Equus caballus
<220> FEATURE:
<223> OTHER INFORMATION: truncated equine (horse) interleukin-4 (IL4)
    receptor (IL4R) encoded by alternate splice
    product, horse soluble IL4R

<400> SEQUENCE: 4

```
Met Gly Cys Leu Cys Pro Gly Leu Thr Leu Pro Val Ser Cys Leu Ile
  1               5                  10                  15

Leu Val Trp Ala Ala Gly Ser Gly Ser Val Lys Val Leu Arg Leu Thr
                 20                  25                  30

Ala Cys Phe Ser Asp Tyr Ile Ser Ala Ser Thr Cys Glu Trp Lys Met
             35                  40                  45

Asp Arg Pro Thr Asn Cys Ser Ala Gln Leu Arg Leu Ser Tyr Gln Leu
         50                  55                  60

Asn Asp Glu Phe Ser Asp Asn Leu Thr Cys Ile Pro Glu Asn Arg Glu
 65                  70                  75                  80

Asp Glu Val Cys Val Cys Arg Met Leu Met Asp Asn Ile Val Ser Glu
                 85                  90                  95

Asp Val Tyr Glu Leu Asp Leu Trp Ala Gly Asn Gln Leu Leu Trp Asn
```

```
              100                 105                 110
Ser Ser Phe Lys Pro Ser Arg His Val Lys Pro Arg Ala Pro Gln Asn
            115                 120                 125

Leu Thr Val His Ala Ile Ser His Thr Trp Leu Leu Thr Trp Ser Asn
        130                 135                 140

Pro Tyr Pro Leu Lys Asn His Leu Trp Ser Glu Leu Thr Tyr Leu Val
145                 150                 155                 160

Asn Ile Ser Lys Glu Asp Pro Thr Asp Phe Lys Ile Tyr Asn Val
                165                 170                 175

Thr Tyr Met Asp Pro Thr Leu Arg Val Thr Ala Ser Thr Leu Lys Ser
            180                 185                 190

Arg Ala Thr Tyr Ser Ala Arg Val Lys Ala Arg Ala Gln Asn Tyr Asn
        195                 200                 205

Ser Thr Trp Ser Glu Trp Ser Pro Ser Thr Thr Trp His Asn Ser Pro
    210                 215                 220

<210> SEQ ID NO 5
<211> LENGTH: 1024
<212> TYPE: DNA
<213> ORGANISM: Canis familiaris
<220> FEATURE:
<223> OTHER INFORMATION: dog soluble interleukin-4 (IL4) receptor (IL4R)
      full length mRNA, dog IL4R mRNA splice variant

<400> SEQUENCE: 5
ctcccaatgg ggtggctttg ctctgggctc acattccctg tgagctgcct ggtcctggtg      60
tgggtggcca gctctgggag tgtgaaggtc ctgcacgagc ccagctgctt ctccgactac     120
atcagcacct ctgtctgtca gtggaagatg gaccatccca ccaactgcag tgccgagctc     180
cgcctgtcct accagctgga ctttatgggg tctgaaaacc acacgtgtgt ccctgagaac     240
cgagaagact cagtgtgcgt gtgcagcatg ccgatagatg acgcggtgga agcggatgtc     300
tatcagctgg acctgtgggc tgggcagcag ctgctatgga gcggctcttt ccagcccagc     360
aagcatgtga agcccaggac ccccggcaac ctcacagttc accccaacat ctcccacacg     420
tggctgctga tgtggacaaa cccataccct actgagaatc acctgcactc tgagctcacc     480
tacatggtca acgtttcgaa tgacaacgac cccgaggact taaagtcta taatgtgacc     540 tacatggggc ccaccctccg cttggcagcc agcaccctca gtctggagc ttcctacagc     600 gcacgtgtga gggcctgggc tcagacctac aacagcacct ggagtgattg gagcccagc      660 accaggtggc ttaactacac ctcctctggc tgagcatccg tgttttgcat tcccatagca     720
gagagtggct ctaactgtgg gttaatggga ttactgactg acctggtgta ctggtcaggg     780
caggtagggc aggctgcggt aacaaatgag cccgcaagtt ctgtgactct tcgctgtagg     840
aatgtatttc ttggtcatgt aaccgtccag cgtgaactca gctggttttg cagggatggg     900 ggagggggc tcctccctgt ggttccatca ttcccttagg gacaaagatt cctaaccttt      960
tcatatcatg gaccccttg gctgtgaacc ccagaatact attttttaaat gtaaaaaata    1020 aaat                                                                 1024

<210> SEQ ID NO 6
<211> LENGTH: 228
<212> TYPE: PRT
<213> ORGANISM: Canis familiaris
<220> FEATURE:
<223> OTHER INFORMATION: dog soluble interleukin-4 (IL4) receptor (IL4R)

<400> SEQUENCE: 6
```

Met Gly Trp Leu Cys Ser Gly Leu Thr Phe Pro Val Ser Cys Leu Val
1               5                   10                  15

Leu Val Trp Val Ala Ser Ser Gly Ser Val Lys Val Leu His Glu Pro
            20                  25                  30

Ser Cys Phe Ser Asp Tyr Ile Ser Thr Ser Val Cys Gln Trp Lys Met
            35                  40                  45

Asp His Pro Thr Asn Cys Ser Ala Glu Leu Arg Leu Ser Tyr Gln Leu
        50                  55                  60

Asp Phe Met Gly Ser Glu Asn His Thr Cys Val Pro Glu Asn Arg Glu
65              70                  75                  80

Asp Ser Val Cys Val Cys Ser Met Pro Ile Asp Asp Ala Val Glu Ala
            85                  90                  95

Asp Val Tyr Gln Leu Asp Leu Trp Ala Gly Gln Gln Leu Leu Trp Ser
            100                 105                 110

Gly Ser Phe Gln Pro Ser Lys His Val Lys Pro Arg Thr Pro Gly Asn
        115                 120                 125

Leu Thr Val His Pro Asn Ile Ser His Thr Trp Leu Leu Met Trp Thr
    130                 135                 140

Asn Pro Tyr Pro Thr Glu Asn His Leu His Ser Glu Leu Thr Tyr Met
145             150                 155                 160

Val Asn Val Ser Asn Asp Asn Pro Glu Asp Phe Lys Val Tyr Asn
            165                 170                 175

Val Thr Tyr Met Gly Pro Thr Leu Arg Leu Ala Ala Ser Thr Leu Lys
            180                 185                 190

Ser Gly Ala Ser Tyr Ser Ala Arg Val Arg Ala Trp Ala Gln Thr Tyr
        195                 200                 205

Asn Ser Thr Trp Ser Asp Trp Ser Pro Ser Thr Arg Trp Leu Asn Tyr
    210                 215                 220

Thr Ser Ser Gly
225

<210> SEQ ID NO 7
<211> LENGTH: 2492
<212> TYPE: DNA
<213> ORGANISM: Canis familiaris
<220> FEATURE:
<223> OTHER INFORMATION: dog interleukin-4 (IL4) receptor (IL4R) partial
      mRNA

<400> SEQUENCE: 7
ctcccaatgg ggtggctttg ctctgggctc acattccctg tgagctgcct ggtcctggtg      60
tgggtggcca gctctgggag tgtgaaggtc ctgcacgagc ccagctgctt ctccgactac     120
atcagcacct ctgtctgtca gtggaagatg gaccatccca ccaactgcag tgccgagctc     180
cgcctgtcct accagctgga ctttatgggg tctgaaaacc acacgtgtgt ccctgagaac     240
cgagaagact cagtgtgcgt gtgcagcatg ccgatagatg acgcggtgga agcggatgtc     300
tatcagctgg acctgtgggc tgggcagcag ctgctatgga gcggctcttt ccagcccagc     360
aagcatgtga agcccaggac ccccggcaac ctcacagttc accccaacat ctcccacacg     420
tggctgctga tgtggacaaa cccatacccct actgagaatc acctgcactc tgagctcacc     480
tacatggtca acgtttcgaa tgacaacgac cccgaggact ttaaagtcta taatgtgacc     540
tacatggggc ccaccctccg cttggcagcc agcaccctca gtctggagc ttcctacagc     600 gcacgtgtga gggcctgggc tcagacctac aacagcacct ggagtgattg gagccccagc     660

-continued

| | |
|---|---|
| accaggtggc ttaactacta cgagccctgg gagcagcacc tgccacttgg cgtcagcatc | 720 |
| tcctgcctcg tcatcctggc catctgcctg tcctgctact tcagtatcat caagattaag | 780 |
| aaaggatggt gggatcagat tcccaaccca gcccacagcc ccctcgtggc catagtcatc | 840 |
| caggactcac aggtgtcgct ctgggggaag cggtcccgag gccaggaacc agccaagtgc | 900 |
| ccacactgga agacttgtct taccaagctc ctgccctgtc tactggagca tggcctgggc | 960 |
| agggaggagg agtcccccaa gactgccaaa aatgggcctc tccaaggtcc yggaaaaccc | 1020 |
| gcgtggtgcc ctgtggaggt cagcaagacg atcctctggc cggagagcat cagcgtggtg | 1080 |
| caatgtgtgg agctctctga ggccccggtg gacaatgaag aggaggagga ggtggaggaa | 1140 |
| gataaagaa gcctctgccc atcgctggag ggcagcgggg gcagcttcca ggagggcaga | 1200 |
| gagggcatcg tggcccggct gacgaaaagc ctcttcctgg accttctcgg cggtgagaat | 1260 |
| ggggggctttt gcccgcaggg cctggaggag tcatgccttc cgcccccctc ggggagtgtg | 1320 |
| ggcgctcaga tgccctgggc tcagttcccg agggccgggc ccgggcggc gcccgagggc | 1380 |
| ccggagcagc ctcgccgccc cgagtccgct cttcaggcct ccccgaccca gagcgcaggc | 1440 |
| agctcggctt tcccagagcc gccccctgtc gtcacagaca accccgcgta ccgcagcttc | 1500 |
| ggcagctttc tgggccagtc ctccgatccc ggcgacggtg actccgaccc agagctggcc | 1560 |
| gatcgccccg gggaagcgga ccccggcatc ccctctgccc ccagccccc ggagccacct | 1620 |
| gccgccctcc agcctgagcc agaaagctgg gagcagatcc tgcgccagag tgtcctccag | 1680 |
| caccgggcag ccccggcccc cggcccgggc cccggcagcg gctaccggga gttcacgtgc | 1740 |
| gccgtgaagc agggcagcgc ccccgacgcc gggggccgg gcttcggccc ttctggggaa | 1800 |
| gcggggtaca aggccttctg cagtctgctc cctggcggtg ccacctgccc ggggacatct | 1860 |
| ggggggtgagg ccggcagtgg ggagggggc tacaagccct tccagagcct cactcctggc | 1920 |
| tgccctgggg cccccacccc agtccctgtc ccctgttca cctttggact ggacacggag | 1980 |
| ccacctggca gccctcagga ctcgctcggc gcaggcagct cccagagca cctgggtgtg | 2040 |
| gagccggcag ggaaggagga ggacagccgt aagaccctgc tggccccaga gcaggccaca | 2100 |
| gaccccctca gggacgacct ggccagtagc atcgtctact cagccctcac ctgccacttg | 2160 |
| tgtggccacc tgaagcagtg gcacgaccag gaggagcgtg gcaaggccca catagtgccc | 2220 |
| agccctgct gtggctgctg ctgtggagac aggtcctcac tcctgctgag ccccctgagg | 2280 |
| gccccgaacg tcctgccagg tggggttctg ctggaggcca gcctctctcc ggcctccctg | 2340 |
| gtaccctcgg gggtctcaaa ggagggcaaa tcctctccgt tctcccagcc tgcctccagc | 2400 |
| agtgctcaga gctcaagcca gacccccaaa aagctggccg tgctttccac agaaaccaca | 2460 |
| tgcatgagcg cttcttagat gcatcctcgg tg | 2492 |

<210> SEQ ID NO 8
<211> LENGTH: 2802
<212> TYPE: DNA
<213> ORGANISM: Felis catus
<220> FEATURE:
<223> OTHER INFORMATION: cat interleukin-4 (IL4) receptor (IL4R) partial mRNA

<400> SEQUENCE: 8

| | |
|---|---|
| atcccgctcg ggcgcgggcg cggcgaatgg accgggggcg cgcaggtgtc ttaggatctc | 60 |
| ccaatgggc ggctttgctc tgggctcacg ttccctgtga gctgtctgat cctgatgtgg | 120 |
| gcggcaggct ctgggagcgt caaggtcctg cgtgcgccca cctgcttctc cgactacttc | 180 |

-continued

| | |
|---|---|
| agcacctccg tctgccagtg aacatggat gcgcccacga actgcagcgc tgagctccgc | 240 |
| ctgtcctacc agctgaactt catggggtcc gaaaaccgca cgtgtgtccc tgagaacgga | 300 |
| gaaggcgcgg cgtgtgcgtg cagcatgctg atggacgact ttgtcgaagc ggacgtgtat | 360 |
| cagctgcacc tgtgggcggg gacgcagctg ctgtggagcg gctccttcaa gcccagcagt | 420 |
| cacgtgaaac ccagggctcc cggaaacctc acggttcacc ccaacgtctc ccacacgtgg | 480 |
| ctgctgaggt ggagcaaccc ttaccccccct gagaaccacc tgcacgccga gctcacctac | 540 |
| atggtcaaca tctcgagtga agacgacccc acggattcca gaatctataa tgtgacctac | 600 |
| atggggccca ccctccgcgt ggcagccagc accctgacgt ctggggcttc ctacagcgca | 660 |
| cgcgtgaggg cctgggctca gagctacaac agcacctgga gcgagtggag ccccagcacc | 720 |
| aagtggctta accactacga gccctgggag cagcacctcc cacttggcgt cagcatctcc | 780 |
| tgccttgtca tcctggccgt ctgcctgtcc tgctacctca gcgtcatcaa gattaagaaa | 840 |
| gaatggtggg accagattcc caaccccgcc cacagccacc tagtggcgat agtcatccgg | 900 |
| gacccacagg tgtcgctgtg ggggaagcgg tcccgaggcc aggaaccagc caagtgccca | 960 |
| cactggaaga cttgtcttag gaagctcctg ccctgtttac tggagcacgg catggaaagg | 1020 |
| aaagaggatc cctccaagat tgccagaaat gggccttcgc agtgttctgg aaaatcagca | 1080 |
| tggtgccccg tggaggtcag caagacgatc ctctggcccg agagcatcag tgtggtgcga | 1140 |
| tgtgtggagc tcctggaggc cccggtggag agcgaggagg aggaggagga ggaggaggaa | 1200 |
| gataaaggga gcttctgccc atcgcctgtg aacctcgagg acagcttcca ggagggccgg | 1260 |
| gagggcatcg cggcccggct gaccgaaagc ctcttcatgg accttctcgg ggttgagaaa | 1320 |
| ggggctttg gccacagggg ctcgctggaa tcgtggtttc ctcctccttc gggaagtgca | 1380 |
| ggtgctcaga tgccctgggc tgagtttccg ggtccggggc cccaggaggc atcgccccag | 1440 |
| ggcaaggagc agcctttcga ccccggtcc gatcctctgg ccactctgcc ccagagccca | 1500 |
| gccagcccga ctttcccaga gacgcccccg gtcgtcacag acaaccccgc ctaccgcagc | 1560 |
| ttcgggacct tccagggccg gtcctcaggt cccggcgagt gtgactcggg ccccgagctg | 1620 |
| gcgggacgcc tgggggaggc ggaccctggc atccccgctg cccccagcc ttcggagccg | 1680 |
| ccttccgcgc tccagcccga ggcagagacc tgggagcaga ttctgcgtca gcgagtcctg | 1740 |
| cagcacaggg gggcccggc cccggccccc ggcagcggct accgagagtt tgtgtgcgcc | 1800 |
| gtgaggcagg gcagcaccca ggacagcagg gtgggggact tcggcccctc ggaggaggcc | 1860 |
| gggtacaagg ccttctcgag tctgctcact agcggtgcc tctgcccaga acgtccgggg | 1920 |
| ggtgaggccg gcagtgggga cggggttac aagcccttcc agagcctcac tcctggctgc | 1980 |
| cctggggccc ccgccccagt ccccgtcccc ctgttcacct tcggactgga cgcggagcca | 2040 |
| cctcattgcc cgcaggactc cccctcccg ggcagctccc cagagccagc ggggaaggcg | 2100 |
| caggacagcc acaagacccc gccggccccg gagcaggccg cagacccctt ccgggacgac | 2160 |
| ctggccagcg gcattgtcta ctcagccctc acctgccacc tgtgtggcca cctgaaacag | 2220 |
| tgtcacggcc aggaggaggg aggcgaggcc caccccgtgg ccagcccctg ctgcggctgc | 2280 |
| tgccgtggag acaggtcctc gccgctggtg agccctctga ggccccgga cccctgcca | 2340 |
| ggtgggggtgc cctggaggc cagcctctct ccagcctccc cggcacccctt ggctgtctca | 2400 |
| gaggagggcc cgccctcct gtgcttccag cctgccctga gcatgctca gctcaagc | 2460 |
| cagacccca aaaggtggc catgctctcc ccagagccca cgtgcacgat ggcttcctag | 2520 |
| gcgcgtgccc gcttgtcact gccgtcttcg agtgagggct gggccttagc ccggcctggg | 2580 |

```
aagtgcctcc cccggaaggc ggctaggctg gaggatttgc aaaagacttg gagaaccctg    2640
ctatgaagct gggaggtggt ctgacctggg ggtacagaga ctgggctcca ccccaccct    2700 cccccagctc ccagccctgg cctggggctc gccacaaccc aagggagtgg agggcacggg    2760
ggagaggccc ctgcgggatc gggagctcct tggggtgcct cg                      2802
```

<210> SEQ ID NO 9
<211> LENGTH: 223
<212> TYPE: PRT
<213> ORGANISM: Felis catus
<220> FEATURE:
<223> OTHER INFORMATION: cat soluble interleukin-4 (IL4) receptor (IL4R)
      partial sequence

<400> SEQUENCE: 9

```
Met Gly Arg Leu Cys Ser Gly Leu Thr Phe Pro Val Ser Cys Leu Ile
  1               5                  10                  15

Leu Met Trp Ala Ala Gly Ser Gly Ser Val Lys Val Leu Arg Ala Pro
             20                  25                  30

Thr Cys Phe Ser Asp Tyr Phe Ser Thr Ser Val Cys Gln Trp Asn Met
         35                  40                  45

Asp Ala Pro Thr Asn Cys Ser Ala Glu Leu Arg Leu Ser Tyr Gln Leu
     50                  55                  60

Asn Phe Met Gly Ser Glu Asn Arg Thr Cys Val Pro Glu Asn Gly Glu
 65                  70                  75                  80

Gly Ala Ala Cys Ala Cys Ser Met Leu Met Asp Asp Phe Val Glu Ala
                 85                  90                  95

Asp Val Tyr Gln Leu His Leu Trp Ala Gly Thr Gln Leu Leu Trp Ser
            100                 105                 110

Gly Ser Phe Lys Pro Ser Ser His Val Lys Pro Arg Ala Pro Gly Asn
        115                 120                 125

Leu Thr Val His Pro Asn Val Ser His Thr Trp Leu Leu Arg Trp Ser
    130                 135                 140

Asn Pro Tyr Pro Pro Glu Asn His Leu His Ala Glu Leu Thr Tyr Met
145                 150                 155                 160

Val Asn Ile Ser Ser Glu Asp Asp Pro Thr Asp Ser Arg Ile Tyr Asn
                165                 170                 175

Val Thr Tyr Met Gly Pro Thr Leu Arg Val Ala Ala Ser Thr Leu Thr
            180                 185                 190

Ser Gly Ala Ser Tyr Ser Ala Arg Val Arg Ala Trp Ala Gln Ser Tyr
        195                 200                 205

Asn Ser Thr Trp Ser Glu Trp Ser Pro Ser Thr Lys Trp Leu Asn
    210                 215                 220
```

<210> SEQ ID NO 10
<211> LENGTH: 818
<212> TYPE: PRT
<213> ORGANISM: Felis catus
<220> FEATURE:
<223> OTHER INFORMATION: cat interleukin-4 (IL4) receptor (IL4R)

<400> SEQUENCE: 10

```
Met Gly Arg Leu Cys Ser Gly Leu Thr Phe Pro Val Ser Cys Leu Ile
  1               5                  10                  15

Leu Met Trp Ala Ala Gly Ser Gly Ser Val Lys Val Leu Arg Ala Pro
             20                  25                  30

Thr Cys Phe Ser Asp Tyr Phe Ser Thr Ser Val Cys Gln Trp Asn Met
```

-continued

```
                35                  40                  45
Asp Ala Pro Thr Asn Cys Ser Ala Glu Leu Arg Leu Ser Tyr Gln Leu
 50                  55                  60
Asn Phe Met Gly Ser Glu Asn Arg Thr Cys Val Pro Glu Asn Gly Glu
 65                  70                  75                  80
Gly Ala Ala Cys Ala Cys Ser Met Leu Met Asp Asp Phe Val Glu Ala
                 85                  90                  95
Asp Val Tyr Gln Leu His Leu Trp Ala Gly Thr Gln Leu Leu Trp Ser
                100                 105                 110
Gly Ser Phe Lys Pro Ser Ser His Val Lys Pro Arg Ala Pro Gly Asn
            115                 120                 125
Leu Thr Val His Pro Asn Val Ser His Thr Trp Leu Leu Arg Trp Ser
            130                 135                 140
Asn Pro Tyr Pro Pro Glu Asn His Leu His Ala Glu Leu Thr Tyr Met
145                 150                 155                 160
Val Asn Ile Ser Ser Glu Asp Pro Thr Asp Ser Arg Ile Tyr Asn
                165                 170                 175
Val Thr Tyr Met Gly Pro Thr Leu Arg Val Ala Ala Ser Thr Leu Thr
                180                 185                 190
Ser Gly Ala Ser Tyr Ser Ala Arg Val Arg Ala Trp Ala Gln Ser Tyr
            195                 200                 205
Asn Ser Thr Trp Ser Glu Trp Ser Pro Ser Thr Lys Trp Leu Asn His
            210                 215                 220
Tyr Glu Pro Trp Glu Gln His Leu Pro Leu Gly Val Ser Ile Ser Cys
225                 230                 235                 240
Leu Val Ile Leu Ala Val Cys Leu Ser Cys Tyr Leu Ser Val Ile Lys
                245                 250                 255
Ile Lys Lys Glu Trp Trp Asp Gln Ile Pro Asn Pro Ala His Ser His
                260                 265                 270
Leu Val Ala Ile Val Ile Arg Asp Pro Gln Val Ser Leu Trp Gly Lys
            275                 280                 285
Arg Ser Arg Gly Gln Glu Pro Ala Lys Cys Pro His Trp Lys Thr Cys
            290                 295                 300
Leu Arg Lys Leu Leu Pro Cys Leu Leu Glu His Gly Met Glu Arg Lys
305                 310                 315                 320
Glu Asp Pro Ser Lys Ile Ala Arg Asn Gly Pro Ser Gln Cys Ser Gly
                325                 330                 335
Lys Ser Ala Trp Cys Pro Val Glu Val Ser Lys Thr Ile Leu Trp Pro
            340                 345                 350
Glu Ser Ile Ser Val Val Arg Cys Val Glu Leu Leu Glu Ala Pro Val
            355                 360                 365
Glu Ser Glu Glu Glu Glu Glu Glu Glu Asp Lys Gly Ser Phe
            370                 375                 380
Cys Pro Ser Pro Val Asn Leu Glu Asp Ser Phe Gln Glu Gly Arg Glu
385                 390                 395                 400
Gly Ile Ala Ala Arg Leu Thr Glu Ser Leu Phe Met Asp Leu Leu Gly
                405                 410                 415
Val Glu Lys Gly Gly Phe Gly Pro Gln Gly Ser Leu Glu Ser Trp Phe
                420                 425                 430
Pro Pro Pro Ser Gly Ser Ala Gly Ala Gln Met Pro Trp Ala Glu Phe
            435                 440                 445
Pro Gly Pro Gly Pro Gln Glu Ala Ser Pro Gln Gly Lys Glu Gln Pro
            450                 455                 460
```

```
Phe Asp Pro Arg Ser Asp Pro Leu Ala Thr Leu Pro Gln Ser Pro Ala
465                 470                 475                 480

Ser Pro Thr Phe Pro Glu Thr Pro Pro Val Val Thr Asp Asn Pro Ala
            485                 490                 495

Tyr Arg Ser Phe Gly Thr Phe Gln Gly Arg Ser Ser Gly Pro Gly Glu
            500                 505                 510

Cys Asp Ser Gly Pro Glu Leu Ala Gly Arg Leu Gly Glu Ala Asp Pro
            515                 520                 525

Gly Ile Pro Ala Ala Pro Gln Pro Ser Glu Pro Pro Ser Ala Leu Gln
        530                 535                 540

Pro Glu Ala Glu Thr Trp Glu Gln Ile Leu Arg Gln Arg Val Leu Gln
545                 550                 555                 560

His Arg Gly Ala Pro Ala Pro Ala Pro Gly Ser Gly Tyr Arg Glu Phe
                565                 570                 575

Val Cys Ala Val Arg Gln Gly Ser Thr Gln Asp Ser Arg Val Gly Asp
            580                 585                 590

Phe Gly Pro Ser Glu Glu Ala Gly Tyr Lys Ala Phe Ser Ser Leu Leu
        595                 600                 605

Thr Ser Gly Ala Val Cys Pro Glu Thr Ser Gly Gly Glu Ala Gly Ser
610                 615                 620

Gly Asp Gly Gly Tyr Lys Pro Phe Gln Ser Leu Thr Pro Gly Cys Pro
625                 630                 635                 640

Gly Ala Pro Ala Pro Val Pro Val Pro Leu Phe Thr Phe Gly Leu Asp
                645                 650                 655

Ala Glu Pro Pro His Cys Pro Gln Asp Ser Pro Leu Pro Gly Ser Ser
            660                 665                 670

Pro Glu Pro Ala Gly Lys Ala Gln Asp Ser His Lys Thr Pro Pro Ala
            675                 680                 685

Pro Glu Gln Ala Ala Asp Pro Leu Arg Asp Asp Leu Ala Ser Gly Ile
        690                 695                 700

Val Tyr Ser Ala Leu Thr Cys His Leu Cys Gly His Leu Lys Gln Cys
705                 710                 715                 720

His Gly Gln Glu Glu Gly Glu Ala His Pro Val Ala Ser Pro Cys
                725                 730                 735

Cys Gly Cys Cys Arg Gly Asp Arg Ser Ser Pro Leu Val Ser Pro Leu
            740                 745                 750

Arg Ala Pro Asp Pro Leu Pro Gly Gly Val Pro Leu Glu Ala Ser Leu
            755                 760                 765

Ser Pro Ala Ser Pro Ala Pro Leu Ala Val Ser Glu Glu Gly Pro Pro
            770                 775                 780

Ser Leu Cys Phe Gln Pro Ala Leu Ser His Ala His Ser Ser Ser Gln
785                 790                 795                 800

Thr Pro Lys Lys Val Ala Met Leu Ser Pro Glu Pro Thr Cys Thr Met
                805                 810                 815

Ala Ser
```

<210> SEQ ID NO 11
<211> LENGTH: 823
<212> TYPE: PRT
<213> ORGANISM: Canis familiaris
<220> FEATURE:
<223> OTHER INFORMATION: dog interleukin-4 (IL4) receptor (IL4R)

<400> SEQUENCE: 11

-continued

```
Met Gly Trp Leu Cys Ser Gly Leu Thr Phe Pro Val Ser Cys Leu Val
 1               5                  10                  15

Leu Val Trp Val Ala Ser Ser Gly Ser Val Lys Val Leu His Glu Pro
            20                  25                  30

Ser Cys Phe Ser Asp Tyr Ile Ser Thr Ser Val Cys Gln Trp Lys Met
            35                  40                  45

Asp His Pro Thr Asn Cys Ser Ala Glu Leu Arg Leu Ser Tyr Gln Leu
     50                  55                  60

Asp Phe Met Gly Ser Glu Asn His Thr Cys Val Pro Glu Asn Arg Glu
 65                  70                  75                  80

Asp Ser Val Cys Val Cys Ser Met Pro Ile Asp Asp Ala Val Glu Ala
                85                  90                  95

Asp Val Tyr Gln Leu Asp Leu Trp Ala Gly Gln Gln Leu Leu Trp Ser
            100                 105                 110

Gly Ser Phe Gln Pro Ser Lys His Val Lys Pro Arg Thr Pro Gly Asn
            115                 120                 125

Leu Thr Val His Pro Asn Ile Ser His Thr Trp Leu Leu Met Trp Thr
            130                 135                 140

Asn Pro Tyr Pro Thr Glu Asn His Leu His Ser Glu Leu Thr Tyr Met
145                 150                 155                 160

Val Asn Val Ser Asn Asp Asn Pro Glu Asp Phe Lys Val Tyr Asn
                165                 170                 175

Val Thr Tyr Met Gly Pro Thr Leu Arg Leu Ala Ala Ser Thr Leu Lys
            180                 185                 190

Ser Gly Ala Ser Tyr Ser Ala Arg Val Arg Ala Trp Ala Gln Thr Tyr
            195                 200                 205

Asn Ser Thr Trp Ser Asp Trp Ser Pro Ser Thr Arg Trp Leu Asn Tyr
210                 215                 220

Tyr Glu Pro Trp Glu Gln His Leu Pro Leu Gly Val Ser Ile Ser Cys
225                 230                 235                 240

Leu Val Ile Leu Ala Ile Cys Leu Ser Cys Tyr Phe Ser Ile Ile Lys
            245                 250                 255

Ile Lys Lys Gly Trp Trp Asp Gln Ile Pro Asn Pro Ala His Ser Pro
            260                 265                 270

Leu Val Ala Ile Val Ile Gln Asp Ser Gln Val Ser Leu Trp Gly Lys
            275                 280                 285

Arg Ser Arg Gly Gln Glu Pro Ala Lys Cys Pro His Trp Lys Thr Cys
            290                 295                 300

Leu Thr Lys Leu Leu Pro Cys Leu Leu Glu His Gly Leu Gly Arg Glu
305                 310                 315                 320

Glu Glu Ser Pro Lys Thr Ala Lys Asn Gly Pro Leu Gln Gly Pro Gly
                325                 330                 335

Lys Pro Ala Trp Cys Pro Val Glu Val Ser Lys Thr Ile Leu Trp Pro
            340                 345                 350

Glu Ser Ile Ser Val Val Gln Cys Val Glu Leu Ser Glu Ala Pro Val
            355                 360                 365

Asp Asn Glu Glu Glu Glu Val Glu Glu Asp Lys Arg Ser Leu Cys
            370                 375                 380

Pro Ser Leu Glu Gly Ser Gly Ser Phe Gln Glu Gly Arg Glu Gly
385                 390                 395                 400

Ile Val Ala Arg Leu Thr Glu Ser Leu Phe Leu Asp Leu Leu Gly Gly
            405                 410                 415

Glu Asn Gly Gly Phe Cys Pro Gln Gly Leu Glu Glu Ser Cys Leu Pro
```

```
                    420             425             430
Pro Pro Ser Gly Ser Val Gly Ala Gln Met Pro Trp Ala Gln Phe Pro
            435                 440                 445
Arg Ala Gly Pro Arg Ala Ala Pro Glu Gly Pro Glu Gln Pro Arg Arg
    450                 455                 460
Pro Glu Ser Ala Leu Gln Ala Ser Pro Thr Gln Ser Ala Gly Ser Ser
465                 470                 475                 480
Ala Phe Pro Glu Pro Pro Val Val Thr Asp Asn Pro Ala Tyr Arg
                485                 490                 495
Ser Phe Gly Ser Phe Leu Gly Gln Ser Ser Asp Pro Gly Asp Gly Asp
            500                 505                 510
Ser Asp Pro Glu Leu Ala Asp Arg Pro Gly Glu Ala Asp Pro Gly Ile
        515                 520                 525
Pro Ser Ala Pro Gln Pro Glu Pro Pro Ala Ala Leu Gln Pro Glu
    530                 535                 540
Pro Glu Ser Trp Glu Gln Ile Leu Arg Gln Ser Val Leu Gln His Arg
545                 550                 555                 560
Ala Ala Pro Ala Pro Gly Pro Gly Pro Gly Ser Gly Tyr Arg Glu Phe
                565                 570                 575
Thr Cys Ala Val Lys Gln Gly Ser Ala Pro Asp Ala Gly Pro Gly
            580                 585                 590
Phe Gly Pro Ser Gly Glu Ala Gly Tyr Lys Ala Phe Cys Ser Leu Leu
        595                 600                 605
Pro Gly Gly Ala Thr Cys Pro Gly Thr Ser Gly Gly Glu Ala Gly Ser
    610                 615                 620
Gly Glu Gly Gly Tyr Lys Pro Phe Gln Ser Leu Thr Pro Gly Cys Pro
625                 630                 635                 640
Gly Ala Pro Thr Pro Val Pro Val Pro Leu Phe Thr Phe Gly Leu Asp
                645                 650                 655
Thr Glu Pro Pro Gly Ser Pro Gln Asp Ser Leu Gly Ala Gly Ser Ser
            660                 665                 670
Pro Glu His Leu Gly Val Glu Pro Ala Gly Lys Glu Glu Asp Ser Arg
        675                 680                 685
Lys Thr Leu Leu Ala Pro Glu Gln Ala Thr Asp Pro Leu Arg Asp Asp
    690                 695                 700
Leu Ala Ser Ser Ile Val Tyr Ser Ala Leu Thr Cys His Leu Cys Gly
705                 710                 715                 720
His Leu Lys Gln Trp His Asp Gln Glu Glu Arg Gly Lys Ala His Ile
                725                 730                 735
Val Pro Ser Pro Cys Cys Gly Cys Cys Cys Gly Asp Arg Ser Ser Leu
            740                 745                 750
Leu Leu Ser Pro Leu Arg Ala Pro Asn Val Leu Pro Gly Gly Val Leu
        755                 760                 765
Leu Glu Ala Ser Leu Ser Pro Ala Ser Leu Val Pro Ser Gly Val Ser
    770                 775                 780
Lys Glu Gly Lys Ser Ser Pro Phe Ser Gln Pro Ala Ser Ser Ser Ala
785                 790                 795                 800
Gln Ser Ser Ser Gln Thr Pro Lys Lys Leu Ala Val Leu Ser Thr Glu
                805                 810                 815
Thr Thr Cys Met Ser Ala Ser
            820

<210> SEQ ID NO 12
```

```
<211> LENGTH: 222
<212> TYPE: PRT
<213> ORGANISM: Artificial Sequence
<220> FEATURE:
<223> OTHER INFORMATION: Description of Artificial Sequence:artificial
      soluble horse IL4R

<400> SEQUENCE: 12

Met Gly Cys Leu Cys Pro Gly Leu Thr Leu Pro Val Ser Cys Leu Ile
 1               5                  10                  15

Leu Val Trp Ala Ala Gly Ser Gly Ser Val Lys Val Leu Arg Leu Thr
                20                  25                  30

Ala Cys Phe Ser Asp Tyr Ile Ser Ala Ser Thr Cys Glu Trp Lys Met
            35                  40                  45

Asp Arg Pro Thr Asn Cys Ser Ala Gln Leu Arg Leu Ser Tyr Gln Leu
        50                  55                  60

Asn Asp Glu Phe Ser Asp Asn Leu Thr Cys Ile Pro Glu Asn Arg Glu
 65                  70                  75                  80

Asp Glu Val Cys Val Cys Arg Met Leu Met Asp Asn Ile Val Ser Glu
                85                  90                  95

Asp Val Tyr Glu Leu Asp Leu Trp Ala Gly Asn Gln Leu Leu Trp Asn
            100                 105                 110

Ser Ser Phe Lys Pro Ser Arg His Val Lys Pro Arg Ala Pro Gln Asn
        115                 120                 125

Leu Thr Val His Ala Ile Ser His Thr Trp Leu Leu Thr Trp Ser Asn
    130                 135                 140

Pro Tyr Pro Leu Lys Asn His Leu Trp Ser Glu Leu Thr Tyr Leu Val
145                 150                 155                 160

Asn Ile Ser Lys Glu Asp Asp Pro Thr Asp Phe Lys Ile Tyr Asn Val
                165                 170                 175

Thr Tyr Met Asp Pro Thr Leu Arg Val Thr Ala Ser Thr Leu Lys Ser
            180                 185                 190

Arg Ala Thr Tyr Ser Ala Arg Val Lys Ala Arg Ala Gln Asn Tyr Asn
        195                 200                 205

Ser Thr Trp Ser Glu Trp Ser Pro Ser Thr Thr Trp His Asn
    210                 215                 220

<210> SEQ ID NO 13
<211> LENGTH: 223
<212> TYPE: PRT
<213> ORGANISM: Artificial Sequence
<220> FEATURE:
<223> OTHER INFORMATION: Description of Artificial Sequence:artificial
      soluble dog IL4R

<400> SEQUENCE: 13

Met Gly Trp Leu Cys Ser Gly Leu Thr Phe Pro Val Ser Cys Leu Val
 1               5                  10                  15

Leu Val Trp Val Ala Ser Ser Gly Ser Val Lys Val Leu His Glu Pro
                20                  25                  30

Ser Cys Phe Ser Asp Tyr Ile Ser Thr Ser Val Cys Gln Trp Lys Met
            35                  40                  45

Asp His Pro Thr Asn Cys Ser Ala Glu Leu Arg Leu Ser Tyr Gln Leu
        50                  55                  60

Asp Phe Met Gly Ser Glu Asn His Thr Cys Val Pro Glu Asn Arg Glu
 65                  70                  75                  80

Asp Ser Val Cys Val Cys Ser Met Pro Ile Asp Ala Val Glu Ala
                85                  90                  95
```

```
Asp Val Tyr Gln Leu Asp Leu Trp Ala Gly Gln Gln Leu Leu Trp Ser
            100                 105                 110

Gly Ser Phe Gln Pro Ser Lys His Val Lys Pro Arg Thr Pro Gly Asn
            115                 120                 125

Leu Thr Val His Pro Asn Ile Ser His Thr Trp Leu Leu Met Trp Thr
        130                 135                 140

Asn Pro Tyr Pro Thr Glu Asn His Leu His Ser Glu Leu Thr Tyr Met
145                 150                 155                 160

Val Asn Val Ser Asn Asp Asn Pro Glu Asp Phe Lys Val Tyr Asn
                165                 170                 175

Val Thr Tyr Met Gly Pro Thr Leu Arg Leu Ala Ala Ser Thr Leu Lys
            180                 185                 190

Ser Gly Ala Ser Tyr Ser Ala Arg Val Arg Ala Trp Ala Gln Thr Tyr
        195                 200                 205

Asn Ser Thr Trp Ser Asp Trp Ser Pro Ser Thr Arg Trp Leu Asn
        210                 215                 220
```

<210> SEQ ID NO 14
<211> LENGTH: 825
<212> TYPE: PRT
<213> ORGANISM: Homo sapiens
<220> FEATURE:
<223> OTHER INFORMATION: human interleukin-4 (IL4) receptor (IL4R)

<400> SEQUENCE: 14

```
Met Gly Trp Leu Cys Ser Gly Leu Leu Phe Pro Val Ser Cys Leu Val
 1               5                  10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
 65                 70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
            115                 120                 125

Leu Thr Val His Thr Asn Val Ser Asp Thr Leu Leu Leu Thr Trp Ser
        130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Cys Tyr
        195                 200                 205

Asn Thr Thr Trp Ser Glu Trp Ser Pro Ser Thr Lys Trp His Asn Ser
    210                 215                 220

Tyr Arg Glu Pro Phe Glu Gln His Leu Leu Leu Gly Val Ser Val Ser
225                 230                 235                 240
```

-continued

```
Cys Ile Val Ile Leu Ala Val Cys Leu Leu Cys Tyr Val Ser Ile Thr
            245                 250                 255
Lys Ile Lys Lys Glu Trp Trp Asp Gln Ile Pro Asn Pro Ala Arg Ser
        260                 265                 270
Arg Leu Val Ala Ile Ile Gln Asp Ala Gln Gly Ser Gln Trp Glu
    275                 280                 285
Lys Arg Ser Arg Gly Gln Glu Pro Ala Lys Cys Pro His Trp Lys Asn
290                 295                 300
Cys Leu Thr Lys Leu Leu Pro Cys Phe Leu Glu His Asn Met Lys Arg
305                 310                 315                 320
Asp Glu Asp Pro His Lys Ala Ala Lys Glu Met Pro Phe Gln Gly Ser
            325                 330                 335
Gly Lys Ser Ala Trp Cys Pro Val Glu Ile Ser Lys Thr Val Leu Trp
            340                 345                 350
Pro Glu Ser Ile Ser Val Val Arg Cys Val Glu Leu Phe Glu Ala Pro
            355                 360                 365
Val Glu Cys Glu Glu Glu Glu Val Glu Glu Glu Lys Gly Ser Phe
    370                 375                 380
Cys Ala Ser Pro Glu Ser Ser Arg Asp Asp Phe Gln Glu Gly Arg Glu
385                 390                 395                 400
Gly Ile Val Ala Arg Leu Thr Glu Ser Leu Phe Leu Asp Leu Leu Gly
            405                 410                 415
Glu Glu Asn Gly Gly Phe Cys Gln Gln Asp Met Gly Glu Ser Cys Leu
            420                 425                 430
Leu Pro Pro Ser Gly Ser Thr Ser Ala His Met Pro Trp Asp Glu Phe
            435                 440                 445
Pro Ser Ala Gly Pro Lys Glu Ala Pro Pro Trp Gly Lys Glu Gln Pro
            450                 455                 460
Leu His Leu Glu Pro Ser Pro Ala Ser Pro Thr Gln Ser Pro Asp
465                 470                 475                 480
Asn Leu Thr Cys Thr Glu Thr Pro Leu Val Ile Ala Gly Asn Pro Ala
            485                 490                 495
Tyr Arg Ser Phe Ser Asn Ser Leu Ser Gln Ser Pro Cys Pro Arg Glu
            500                 505                 510
Leu Gly Pro Asp Pro Leu Leu Ala Arg His Leu Glu Glu Val Glu Pro
            515                 520                 525
Glu Met Pro Cys Val Pro Gln Leu Ser Glu Pro Thr Thr Val Pro Gln
530                 535                 540
Pro Glu Pro Glu Thr Trp Glu Gln Ile Leu Arg Arg Asn Val Leu Gln
545                 550                 555                 560
His Gly Ala Ala Ala Pro Val Ser Ala Pro Thr Ser Gly Tyr Gln
            565                 570                 575
Glu Phe Val His Ala Val Glu Gln Gly Gly Thr Gln Ala Ser Ala Val
            580                 585                 590
Val Gly Leu Gly Pro Pro Gly Glu Ala Gly Tyr Lys Ala Phe Ser Ser
            595                 600                 605
Leu Leu Ala Ser Ser Ala Val Ser Pro Glu Lys Cys Gly Phe Gly Ala
    610                 615                 620
Ser Ser Gly Glu Glu Gly Tyr Lys Pro Phe Gln Asp Leu Ile Pro Gly
625                 630                 635                 640
Cys Pro Gly Asp Pro Ala Pro Val Pro Val Pro Leu Phe Thr Phe Gly
            645                 650                 655
```

-continued

```
Leu Asp Arg Glu Pro Pro Arg Ser Pro Gln Ser Ser His Leu Pro Ser
            660                 665                 670
Ser Ser Pro Glu His Leu Gly Leu Glu Pro Gly Glu Lys Val Glu Asp
        675                 680                 685
Met Pro Lys Pro Pro Leu Pro Gln Glu Gln Ala Thr Asp Pro Leu Val
    690                 695                 700
Asp Ser Leu Gly Ser Gly Ile Val Tyr Ser Ala Leu Thr Cys His Leu
705                 710                 715                 720
Cys Gly His Leu Lys Gln Cys His Gly Gln Glu Asp Gly Gly Gln Thr
                725                 730                 735
Pro Val Met Ala Ser Pro Cys Cys Gly Cys Cys Cys Gly Asp Arg Ser
            740                 745                 750
Ser Pro Pro Thr Thr Pro Leu Arg Ala Pro Asp Pro Ser Pro Gly Gly
        755                 760                 765
Val Pro Leu Glu Ala Ser Leu Cys Pro Ala Ser Leu Ala Pro Ser Gly
    770                 775                 780
Ile Ser Glu Lys Ser Lys Ser Ser Ser Phe His Pro Ala Pro Gly
785                 790                 795                 800
Asn Ala Gln Ser Ser Ser Gln Thr Pro Lys Ile Val Asn Phe Val Ser
                805                 810                 815
Val Gly Pro Thr Tyr Met Arg Val Ser
            820                 825

<210> SEQ ID NO 15
<211> LENGTH: 809
<212> TYPE: PRT
<213> ORGANISM: Equus caballus
<220> FEATURE:
<223> OTHER INFORMATION: horse interleukin-4 (IL4) receptor (IL4R)
      polymorphism A572V

<400> SEQUENCE: 15

Met Gly Cys Leu Cys Pro Gly Leu Thr Leu Pro Val Ser Cys Leu Ile
1               5                   10                  15
Leu Val Trp Ala Ala Gly Ser Gly Ser Val Lys Val Leu Arg Leu Thr
            20                  25                  30
Ala Cys Phe Ser Asp Tyr Ile Ser Ala Ser Thr Cys Glu Trp Lys Met
        35                  40                  45
Asp Arg Pro Thr Asn Cys Ser Ala Gln Leu Arg Leu Ser Tyr Gln Leu
    50                  55                  60
Asn Asp Glu Phe Ser Asp Asn Leu Thr Cys Ile Pro Glu Asn Arg Glu
65                  70                  75                  80
Asp Glu Val Cys Val Cys Arg Met Leu Met Asp Asn Ile Val Ser Glu
                85                  90                  95
Asp Val Tyr Glu Leu Asp Leu Trp Ala Gly Asn Gln Leu Leu Trp Asn
            100                 105                 110
Ser Ser Phe Lys Pro Ser Arg His Val Lys Pro Arg Ala Pro Gln Asn
        115                 120                 125
Leu Thr Val His Ala Ile Ser His Thr Trp Leu Leu Thr Trp Ser Asn
    130                 135                 140
Pro Tyr Pro Leu Lys Asn His Leu Trp Ser Glu Leu Thr Tyr Leu Val
145                 150                 155                 160
Asn Ile Ser Lys Glu Asp Asp Pro Thr Asp Phe Lys Ile Tyr Asn Val
                165                 170                 175
Thr Tyr Met Asp Pro Thr Leu Arg Val Thr Ala Ser Thr Leu Lys Ser
            180                 185                 190
```

```
Arg Ala Thr Tyr Ser Ala Arg Val Lys Ala Arg Ala Gln Asn Tyr Asn
            195                 200                 205

Ser Thr Trp Ser Glu Trp Ser Pro Ser Thr Thr Trp His Asn Tyr Tyr
    210                 215                 220

Glu Gln Pro Leu Glu Gln Arg Leu Pro Leu Gly Val Ser Ile Ser Cys
225                 230                 235                 240

Val Val Ile Leu Ala Ile Cys Leu Ser Cys Tyr Phe Ser Ile Ile Lys
                245                 250                 255

Ile Lys Lys Glu Trp Trp Asp Gln Ile Pro Asn Pro Ala His Ser Pro
            260                 265                 270

Leu Val Ala Ile Val Leu Gln Asp Ser Gln Val Ser Leu Trp Gly Lys
        275                 280                 285

Gln Ser Arg Gly Gln Glu Pro Ala Lys Cys Pro Arg Trp Lys Thr Cys
    290                 295                 300

Leu Thr Lys Leu Leu Pro Cys Leu Leu Glu His Gly Leu Gln Lys Glu
305                 310                 315                 320

Glu Asp Ser Ser Lys Thr Val Arg Asn Gly Pro Phe Gln Ser Pro Gly
                325                 330                 335

Lys Ser Ala Trp His Thr Val Glu Val Asn His Thr Ile Leu Arg Pro
            340                 345                 350

Glu Ile Ile Ser Val Val Pro Cys Val Glu Leu Cys Glu Ala Gln Val
        355                 360                 365

Glu Ser Glu Glu Glu Glu Val Glu Glu Asp Arg Gly Ser Phe Cys Pro
    370                 375                 380

Ser Pro Glu Ser Ser Gly Ser Gly Phe Gln Glu Gly Arg Glu Gly Val
385                 390                 395                 400

Ala Ala Arg Leu Thr Glu Ser Leu Phe Leu Gly Leu Leu Gly Ala Glu
                405                 410                 415

Asn Gly Ala Leu Gly Glu Ser Cys Leu Leu Pro Pro Leu Gly Ser Ala
            420                 425                 430

His Met Pro Trp Ala Arg Ile Ser Ser Ala Gly Pro Gln Glu Ala Ala
        435                 440                 445

Ser Gln Gly Glu Glu Gln Pro Leu Asn Pro Glu Ser Asn Pro Leu Ala
    450                 455                 460

Thr Leu Thr Gln Ser Pro Gly Ser Leu Ala Phe Thr Glu Ala Pro Ala
465                 470                 475                 480

Val Val Ala Asp Asn Pro Ala Tyr Arg Ser Phe Ser Asn Ser Leu Ser
                485                 490                 495

Gln Pro Arg Gly Pro Gly Glu Leu Asp Ser Asp Pro Gln Leu Ala Glu
            500                 505                 510

His Leu Gly Gln Val Asp Pro Ser Ile Pro Ser Ala Pro Gln Pro Ser
        515                 520                 525

Glu Pro Pro Thr Ala Leu Gln Pro Glu Pro Glu Thr Trp Glu Gln Met
    530                 535                 540

Leu Arg Gln Ser Val Leu Gln Gln Gly Ala Ala Pro Ala Pro Ala Ser
545                 550                 555                 560

Ala Pro Thr Gly Gly Tyr Arg Glu Phe Ala Gln Ala Val Lys Gln Gly
                565                 570                 575

Gly Gly Ala Ala Gly Ser Gly Pro Ser Gly Glu Ala Gly Tyr Lys Ala
            580                 585                 590

Phe Ser Ser Leu Leu Ala Gly Ser Ala Val Cys Pro Gly Gln Ser Gly
        595                 600                 605
```

-continued

```
Val Glu Ala Ser Ser Gly Glu Gly Gly Tyr Arg Pro Tyr Glu Ser Pro
    610                 615                 620
Asp Pro Gly Ala Pro Ala Pro Val Pro Val Pro Leu Phe Thr Phe Gly
625                 630                 635                 640
Leu Asp Val Glu Pro Pro His Ser Pro Gln Asn Ser Leu Leu Pro Gly
                645                 650                 655
Gly Ser Pro Glu Leu Pro Gly Pro Glu Pro Thr Val Lys Gly Glu Asp
            660                 665                 670
Pro Arg Lys Pro Leu Leu Ser Ala Gln Gln Ala Thr Asp Ser Leu Arg
        675                 680                 685
Asp Asp Leu Gly Ser Gly Ile Val Tyr Ser Ala Leu Thr Cys His Leu
    690                 695                 700
Cys Gly His Leu Lys Gln Cys His Gly Gln Glu His Gly Glu Ala
705                 710                 715                 720
His Thr Val Ala Ser Pro Cys Cys Gly Cys Cys Cys Gly Asp Arg Ser
                725                 730                 735
Ser Pro Pro Val Ser Pro Val Arg Ala Leu Asp Pro Pro Gly Gly
            740                 745                 750
Val Pro Leu Glu Ala Gly Leu Ser Leu Ala Ser Leu Gly Ser Leu Gly
        755                 760                 765
Leu Ser Glu Glu Arg Lys Pro Ser Leu Phe Phe Gln Pro Ala Pro Gly
    770                 775                 780
Asn Ala Gln Ser Ser Ser Gln Thr Pro Leu Thr Val Ala Met Leu Ser
785                 790                 795                 800
Thr Gly Pro Thr Cys Thr Ser Ala Ser
                805
```

```
<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence:
      extracellular WSXWS motif
<220> FEATURE:
<221> NAME/KEY: MOD_RES
<222> LOCATION: (3)
<223> OTHER INFORMATION: Xaa = any amino acid

<400> SEQUENCE: 16

Trp Ser Xaa Trp Ser
  1               5

<210> SEQ ID NO 17
<211> LENGTH: 1053
<212> TYPE: DNA
<213> ORGANISM: Canis familiaris
<220> FEATURE:
<223> OTHER INFORMATION: dog interleukin-4 (IL4) receptor (IL4R) partial
      mRNA

<400> SEQUENCE: 17
ctcccaatgg ggtggctttg ctctgggctc acattccctg tgagctgcct ggtcctggtg      60
tgggtggcca gctctgggag tgtgaaggtc ctgcacgagc ccagctgctt ctccgactac     120
atcagcaccc tgtctctgtca gtggaagatg gaccatccca ccaactgcag tgccgagctc     180
cgcctgtcct accagctgga ctttatgggg tctgaaaacc acacgtgtgt ccctgagaac     240
cgagaagact cagtgtgcgt gtgcagcatg ccgatagatg acgcggtgga agcggatgtc     300
tatcagctgg acctgtgggc tgggcagcag ctgctatgga gcggctcttt ccagcccagc     360
```

```
aagcatgtga agcccaggac ccccggcaac ctcacagttc accccaacat ctcccacacg    420
tggctgctga tgtggacaaa cccatacct actgagaatc acctgcactc tgagctcacc     480
tacatggtca acgtttcgaa tgacaacgac cccgaggact ttaaagtcta atgtgacc       540 tacatgggggc ccaccctccg cttggcagcc agcaccctca agtctggagc ttcctacagc   600
gcacgtgtga gggcctgggc tcagacctac aacagcacct ggagtgattg gagccccagc    660
accaggtggc ttaactacta cgagccctgg gagcagcacc tgccacttgg cgtcagcatc    720
tcctgcctcg tcatcctggc catctgcctg tcctgctact tcagtatcat caagattaag    780
aaaggatggt gggatcagat tcccaaccca gcccacagcc ccctcgtggc catagtcatc    840
caggactcac aggtgtcgct ctgggggaag cggtcccgag ccaggaacc agccaagtgc     900 ccacactgga agacttgtct taccaagctc ctgccctgtc tactggagca tggcctgggc    960
agggaggagg agtcccccaa gactgccaaa aatgggcctc tccaaggtcc tggaaaaccc   1020
gcgtggtgcc ctgtggaggt cagcaagacg atc                                1053
```

<210> SEQ ID NO 18
<211> LENGTH: 223
<212> TYPE: PRT
<213> ORGANISM: Felis catus
<220> FEATURE:
<223> OTHER INFORMATION: cat soluble interleukin-4 (IL4) receptor (IL4R)
<220> FEATURE:
<221> NAME/KEY: MOD_RES
<222> LOCATION: (87)
<223> OTHER INFORMATION: Xaa = any amino acid

<400> SEQUENCE: 18

```
Met Gly Arg Leu Cys Ser Gly Leu Thr Phe Pro Val Ser Cys Leu Ile
  1               5                  10                  15

Leu Met Trp Ala Ala Gly Ser Gly Ser Val Lys Val Leu Arg Ala Pro
                 20                  25                  30

Thr Cys Phe Ser Asp Tyr Phe Ser Thr Ser Val Cys Gln Trp Asn Met
             35                  40                  45

Asp Ala Pro Thr Asn Cys Ser Ala Glu Leu Arg Leu Ser Tyr Gln Leu
         50                  55                  60

Asn Phe Met Gly Ser Glu Asn Arg Thr Cys Val Pro Glu Asn Gly Glu
 65                  70                  75                  80

Gly Ala Ala Cys Ala Cys Xaa Met Leu Met Asp Asp Phe Val Glu Ala
                 85                  90                  95

Asp Val Tyr Gln Leu His Leu Trp Ala Gly Thr Gln Leu Leu Trp Ser
            100                 105                 110

Gly Ser Phe Lys Pro Ser His Val Lys Pro Arg Ala Pro Gly Asn
        115                 120                 125

Leu Thr Val His Pro Asn Val Ser His Thr Trp Leu Leu Arg Trp Ser
    130                 135                 140

Asn Pro Tyr Pro Pro Glu Asn His Leu His Ala Glu Leu Thr Tyr Met
145                 150                 155                 160

Val Asn Ile Ser Ser Glu Asp Asp Pro Thr Asp Ser Arg Ile Tyr Asn
                165                 170                 175

Val Thr Tyr Met Gly Pro Thr Leu Arg Val Ala Ala Ser Thr Leu Thr
            180                 185                 190

Ser Gly Ala Ser Tyr Ser Ala Arg Val Arg Ala Trp Ala Gln Ser Tyr
        195                 200                 205

Asn Ser Thr Trp Ser Glu Trp Ser Pro Ser Thr Lys Trp Leu Asn
```

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence:His-6 tag

<400> SEQUENCE: 19

His His His His His His
 1               5

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:PCR
      amplification primer IL4R 284f

<400> SEQUENCE: 20
gactacatca gcatctccac                                              20

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence:PCR
      amplification primer IL4R 505r

<400> SEQUENCE: 21
cttgaaggag ctgttccac                                               19

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence:nested PCR
      amplification gene-specific primer IL4R 580f

<400> SEQUENCE: 22
aacatctcca aggacgac                                                18

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:nested PCR
      amplification gene-specific primer IL4R 619f

<400> SEQUENCE: 23
acaacgtgac ctacatggac                                              20

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence:PCR
      amplification primer AF, cycle sequencing reaction
      primer AF

<400> SEQUENCE: 24

-continued

```
aagctcctgc cctgtttact g                                          21
```

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence:PCR
      amplification primer CR, cycle sequencing reaction
      primer CR

<400> SEQUENCE: 25

```
ggaccgcagc aaccagag                                              18
```

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:cycle
      sequencing reaction primer AR

<400> SEQUENCE: 26

```
gctgtgggtc tgagtcaagc                                            20
```

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence:cycle
      sequencing reaction primer BF

<400> SEQUENCE: 27

```
tcaacccaga gtcaaatcct ctg                                        23
```

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence:cycle
      sequencing reaction primer BR

<400> SEQUENCE: 28

```
tcctctccct tcaccgtcg                                             19
```

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence:cycle
      sequencing reaction primer CF

<400> SEQUENCE: 29

```
cctatgagag ccccgacc                                              18
```

<210> SEQ ID NO 30
<211> LENGTH: 12
<212> TYPE: DNA
<213> ORGANISM: Artificial Sequence
<220> FEATURE:
<223> OTHER INFORMATION: Description of Artificial Sequence:nested PCR
      amplification Exon 3 donor sequence

<400> SEQUENCE: 30

```
cggcaggctc tg                                                    12

<210> SEQ ID NO 31
<211> LENGTH: 12
<212> TYPE: DNA
<213> ORGANISM: Artificial Sequence
<220> FEATURE:
<223> OTHER INFORMATION: Description of Artificial Sequence:nested PCR
      amplification Exon 4 acceptor sequence

<400> SEQUENCE: 31
ggagcgttaa gg                                                    12

<210> SEQ ID NO 32
<211> LENGTH: 12
<212> TYPE: DNA
<213> ORGANISM: Artificial Sequence
<220> FEATURE:
<223> OTHER INFORMATION: Description of Artificial Sequence:nested PCR
      amplification Exon 4 donor sequence

<400> SEQUENCE: 32
cgagttctct ga                                                    12

<210> SEQ ID NO 33
<211> LENGTH: 12
<212> TYPE: DNA
<213> ORGANISM: Artificial Sequence
<220> FEATURE:
<223> OTHER INFORMATION: Description of Artificial Sequence:nested PCR
      amplification Exon 5 acceptor sequence

<400> SEQUENCE: 33
caacctcacg tg                                                    12

<210> SEQ ID NO 34
<211> LENGTH: 12
<212> TYPE: DNA
<213> ORGANISM: Artificial Sequence
<220> FEATURE:
<223> OTHER INFORMATION: Description of Artificial Sequence:nested PCR
      amplification Exon 5 donor sequence

<400> SEQUENCE: 34
ccagccggca cg                                                    12

<210> SEQ ID NO 35
<211> LENGTH: 12
<212> TYPE: DNA
<213> ORGANISM: Artificial Sequence
<220> FEATURE:
<223> OTHER INFORMATION: Description of Artificial Sequence:nested PCR
      amplification Exon 6 acceptor sequence

<400> SEQUENCE: 35
tgaaacccag gg                                                    12

<210> SEQ ID NO 36
<211> LENGTH: 12
<212> TYPE: DNA
<213> ORGANISM: Artificial Sequence
<220> FEATURE:
<223> OTHER INFORMATION: Description of Artificial Sequence:nested PCR
      amplification Exon 6 donor sequence

<400> SEQUENCE: 36 gacccacgg ac                                                     12
```

<210> SEQ ID NO 37
<211> LENGTH: 12
<212> TYPE: DNA
<213> ORGANISM: Artificial Sequence
<220> FEATURE:
<223> OTHER INFORMATION: Description of Artificial Sequence:nested PCR amplification Exon 7 acceptor sequence

<400> SEQUENCE: 37
ttcaaaatct ac                                                         12

<210> SEQ ID NO 38
<211> LENGTH: 12
<212> TYPE: DNA
<213> ORGANISM: Artificial Sequence
<220> FEATURE:
<223> OTHER INFORMATION: Description of Artificial Sequence:nested PCR amplification Exon 7 donor sequence

<400> SEQUENCE: 38
cgtggcataa ct                                                         12

<210> SEQ ID NO 39
<211> LENGTH: 12
<212> TYPE: DNA
<213> ORGANISM: Artificial Sequence
<220> FEATURE:
<223> OTHER INFORMATION: Description of Artificial Sequence:nested PCR amplification Exon 8 acceptor sequence

<400> SEQUENCE: 39 cccccctgaac tc                                                        12

<210> SEQ ID NO 40
<211> LENGTH: 11
<212> TYPE: DNA
<213> ORGANISM: Artificial Sequence
<220> FEATURE:
<223> OTHER INFORMATION: Description of Artificial Sequence:nested PCR amplification Exon 8 donor sequence
<220> FEATURE:
<221> NAME/KEY: modified_base
<222> LOCATION: (11)
<223> OTHER INFORMATION: a at position 11 is repeated an unspecified number of times, (A)-n

<400> SEQUENCE: 40
cttttgcaat a                                                          11

<210> SEQ ID NO 41
<211> LENGTH: 12
<212> TYPE: DNA
<213> ORGANISM: Artificial Sequence
<220> FEATURE:
<223> OTHER INFORMATION: Description of Artificial Sequence:nested PCR amplification Exon 9 acceptor sequence

<400> SEQUENCE: 41
actacgagca gc                                                         12

<210> SEQ ID NO 42
<211> LENGTH: 12
<212> TYPE: DNA
<213> ORGANISM: Artificial Sequence
<220> FEATURE:
<223> OTHER INFORMATION: Description of Artificial Sequence:nested PCR amplification Exon 9 donor sequence

<400> SEQUENCE: 42
cagcatcatc aa                                                          12

<210> SEQ ID NO 43
<211> LENGTH: 12
<212> TYPE: DNA
<213> ORGANISM: Artificial Sequence
<220> FEATURE:
<223> OTHER INFORMATION: Description of Artificial Sequence:nested PCR
      amplification Exon 10 acceptor sequence

<400> SEQUENCE: 43
gattaagaaa ga                                                          12

<210> SEQ ID NO 44
<211> LENGTH: 12
<212> TYPE: DNA
<213> ORGANISM: Artificial Sequence
<220> FEATURE:
<223> OTHER INFORMATION: Description of Artificial Sequence:nested PCR
      amplification Exon 10 donor sequence

<400> SEQUENCE: 44
caggattctc ag                                                          12

<210> SEQ ID NO 45
<211> LENGTH: 12
<212> TYPE: DNA
<213> ORGANISM: Artificial Sequence
<220> FEATURE:
<223> OTHER INFORMATION: Description of Artificial Sequence:nested PCR
      amplification Exon 11 acceptor sequence

<400> SEQUENCE: 45
gtgtcactgt gg                                                          12

<210> SEQ ID NO 46
<211> LENGTH: 12
<212> TYPE: DNA
<213> ORGANISM: Artificial Sequence
<220> FEATURE:
<223> OTHER INFORMATION: Description of Artificial Sequence:nested PCR
      amplification Exon 11 donor sequence

<400> SEQUENCE: 46
agccaagtgc cc                                                          12

<210> SEQ ID NO 47
<211> LENGTH: 12
<212> TYPE: DNA
<213> ORGANISM: Artificial Sequence
<220> FEATURE:
<223> OTHER INFORMATION: Description of Artificial Sequence:nested PCR
      amplification Exon 12 acceptor sequence

<400> SEQUENCE: 47
acgctggaag ac                                                          12

<210> SEQ ID NO 48
<211> LENGTH: 11
<212> TYPE: DNA
<213> ORGANISM: Artificial Sequence
<220> FEATURE:
<223> OTHER INFORMATION: Description of Artificial Sequence:nested PCR
      amplification Exon 12 donor sequence
<220> FEATURE:

```
<221> NAME/KEY: modified_base
<222> LOCATION: (11)
<223> OTHER INFORMATION: a at position 11 is repeated an unspecified
      number of times, (A)-n

<400> SEQUENCE: 48
tctttctctc a                                                           11
```